(12) United States Patent
Sarhan et al.

(10) Patent No.: US 10,548,495 B2
(45) Date of Patent: Feb. 4, 2020

(54) CONTACTLESS OR NON-INVASIVE PHYSICAL PROPERTIES MEASUREMENT INSTRUMENT USING EDDY CURRENT-REDUCED HIGH Q RESONANT CIRCUIT PROBE

(71) Applicant: Sameh Sarhan, Santa Clara, CA (US)

(72) Inventors: Sameh Sarhan, Santa Clara, CA (US); Lawrence Herbert Zuckerman, Livermore, CA (US); Jihad Naja, San Jose, CA (US); David VanValen, Sunnyvale, CA (US)

(73) Assignee: Xtrava Inc., Santa Clara, CA (US)

( * ) Notice: Subject to any disclaimer, the term of this patent is extended or adjusted under 35 U.S.C. 154(b) by 737 days.

(21) Appl. No.: 15/082,638

(22) Filed: Mar. 28, 2016

(65) Prior Publication Data
US 2017/0042437 A1 Feb. 16, 2017

Related U.S. Application Data

(60) Provisional application No. 62/141,272, filed on Apr. 1, 2015.

(51) Int. Cl.
| | | |
|---|---|---|
| A61B 5/04 | (2006.01) | |
| A61B 5/0245 | (2006.01) | |
| A61B 5/08 | (2006.01) | |
| A61B 8/08 | (2006.01) | |
| A61B 5/0402 | (2006.01) | |
| A61B 5/145 | (2006.01) | |
| A61B 5/00 | (2006.01) | |

(52) U.S. Cl.
CPC ........ *A61B 5/04005* (2013.01); *A61B 5/0245* (2013.01); *A61B 5/0816* (2013.01); *A61B 8/0883* (2013.01); *A61B 5/0402* (2013.01); *A61B 5/14532* (2013.01); *A61B 5/6804* (2013.01); *A61B 5/7267* (2013.01); *A61B 2560/0209* (2013.01)

(58) Field of Classification Search
CPC ................................... A61B 5/04005
USPC ....................................... 600/408
See application file for complete search history.

(56) References Cited

U.S. PATENT DOCUMENTS

| | | | |
|---|---|---|---|
| 2008/0234534 A1* | 9/2008 | Mikas ...................... | A61N 2/02 600/14 |
| 2009/0306524 A1* | 12/2009 | Muhlsteff .............. | A61B 5/021 600/485 |
| 2011/0190849 A1* | 8/2011 | Faltys ................ | A61N 1/36053 607/50 |
| 2011/0263925 A1* | 10/2011 | Bratton .................. | A61N 2/004 600/14 |
| 2013/0303924 A1* | 11/2013 | Rosell Ferrer ....... | A61B 5/0522 600/508 |

(Continued)

OTHER PUBLICATIONS

Guardo et al., Contactless Measurement of Thoracic Conductivity Changes by Magnetic Induction, Proceedings 19th International Conference—IEEE/EMBS, pp. 2450-2453, 1997.†

*Primary Examiner* — Jason C Olson

(57) ABSTRACT

Eddy current measurement systems for a variety of biometric and other applications, where the target composition and/or other aspects cause relatively small eddy current losses, thus requiring a very high Q tuned circuit probe, and where ultra-miniature and ultra-low power products are required for convenient, non-invasive, and intrinsically safe wearable use.

3 Claims, 16 Drawing Sheets

(56) References Cited

U.S. PATENT DOCUMENTS

| | | | |
|---|---|---|---|
| 2013/0314081 A1* | 11/2013 | Igney | G01N 27/023 324/239 |
| 2015/0065841 A1* | 3/2015 | Lee | A61B 5/053 600/388 |
| 2015/0065842 A1* | 3/2015 | Lee | A61B 5/04085 600/388 |
| 2018/0143150 A1* | 5/2018 | Bezemer | A61B 5/721 |

\* cited by examiner
† cited by third party

CONTACTLESS OR NON-INVASIVE PHYSICAL PROPERTIES MEASUREMENT INSTRUMENT USING EDDY CURRENT-REDUCED HIGH Q RESONANT CIRCUIT PROBE

CROSS-REFERENCE TO RELATED APPLICATION

Priority is claimed under 37 CFR 1.78 and 35 USC 119(e) to U.S. Provisional Application 62/141,272 (XT1503311), filed 1 Apr. 2015), which is incorporated by reference.

TECHNICAL FIELD

This disclosure relates generally to contactless measurements of material properties, and distance, and orientation of objects, when eddy currents are induced in them by locally generated AC magnetic fields. More specifically, this disclosure relates to non-invasive measurement of internal bodily properties and functions, detected by effects on impedance of a very high Q parallel tuned circuit energized with extremely low power alternating currents in the 2 MHz to 20 MHz frequency range.

BACKGROUND

For some years, there have appeared on the market a large number of products that monitor vital signs to track disease states. More recently, there has been a shift in emphasis to monitor the vital signs of individuals for whom there is no suspected illness, but for early indications of health problems. Examples of such vital signs are heart rate and motion, blood pressure, and respiration rate. Part of the need is to provide measurements for a period of hours that may span a variety of activities, such as relaxation, physical exercise, and stressful mental activities. Such measurements can be recorded automatically for later analysis, and in some cases, even be accompanied by alarms when there are readings that do not fall within selected limits.

In order for such products to appeal to vast numbers of individuals who are seemingly "well", they need to be as convenient and unobtrusive as possible, and intrinsically safe. Low cost, small size, light-weight, concealed or ordinary in appearance, ultra-low power consumption, non-invasive, and effortless use are features that will result in the general population enjoying the benefits of extended periods of vital signs monitoring.

Stand-alone wristwatch heart rate instruments, readily available for some years, are not convenient for continuous monitoring; as they require the user to hold the instrument with the opposite hand. Other wearable heart rate instruments are hands free, but they require a harness that goes around the upper torso, and power consumption is considerable.

Existing wearable monitoring products perform a single function, forcing the user to purchase, manage and maintain a separate product for each type of measurement. Hands free heart and respiration rate equipment using eddy currents have been developed, but they are too bulky and require too much power to be successful in the market place discussed above.

The embodiments described in the instant disclosure meet all commercial requirements for size, cost, weight, speed, convenience, power-drain and measurement accuracy. Moreover, for medical applications, eddy current density and power dissipation within the body are far below recognized safety limits. It is shown in the instant document that a fully functioning eddy current instrument here invented will induce within the human body about 5% of the current density amount stated as the safety limit by ICNIRP.

BRIEF DESCRIPTION OF DRAWINGS

For a more complete understanding of this disclosure and its features, reference is now made to the following description, taken in conjunction with the accompanying drawings, in which.

DETAILED DESCRIPTION

The various figures, discussed below, and the various embodiments used to describe the principles of the present invention in this patent document are by way of illustration only and should not be construed in any way to limit the scope of the invention. Those skilled in the art will understand that the principles of the invention may be implemented in any type of suitably arranged device or system.

In general, this disclosure describes the functions and basic design of eddy current measurement instrument systems that obtain information related to the composition and/or motion of conductive objects, such as those located within biological tissues.

The applications for contactless eddy current measurements in this disclosure differ from those that are prevalent today. The prevalent applications, normally for industrial control, use this general method to measure the position or distance of objects ("targets") that are made from highly conductive materials, such as metals. Such materials, when close by, have relatively large eddy currents induced in them, which in turn result in large responses at the probe. The applications in this disclosure often involve target materials having relatively poor conductivity, causing probe response to be minimal, thus requiring special design features, such as high Quality Factor ("Q") probe configuration, signal processing and machine learning methods that filter noise and reduce artifacts.

There are many applications of eddy current measurements that could be considered improvements over other methods. Most of these applications benefit from the non-contact, non-invasive, and/or convenience of this approach. For instance, there are strong indications detailed in numerous scholarly scientific and engineering articles that magnetic eddy current measurements within the human body—which detect motions, volume, and transient physical properties of structure, internal organs, and fluids—can provide useful data on or in support of at least electrocardiography, echocardiography, and blood glucometry. Also covered in these articles are blood flow, heart rate, respiration rate, and the instant inventors verified the latter two categories. Other articles report on favorable properties measurement results with many other organic and inorganic objects and substances that conduct electricity.

Figure 1:
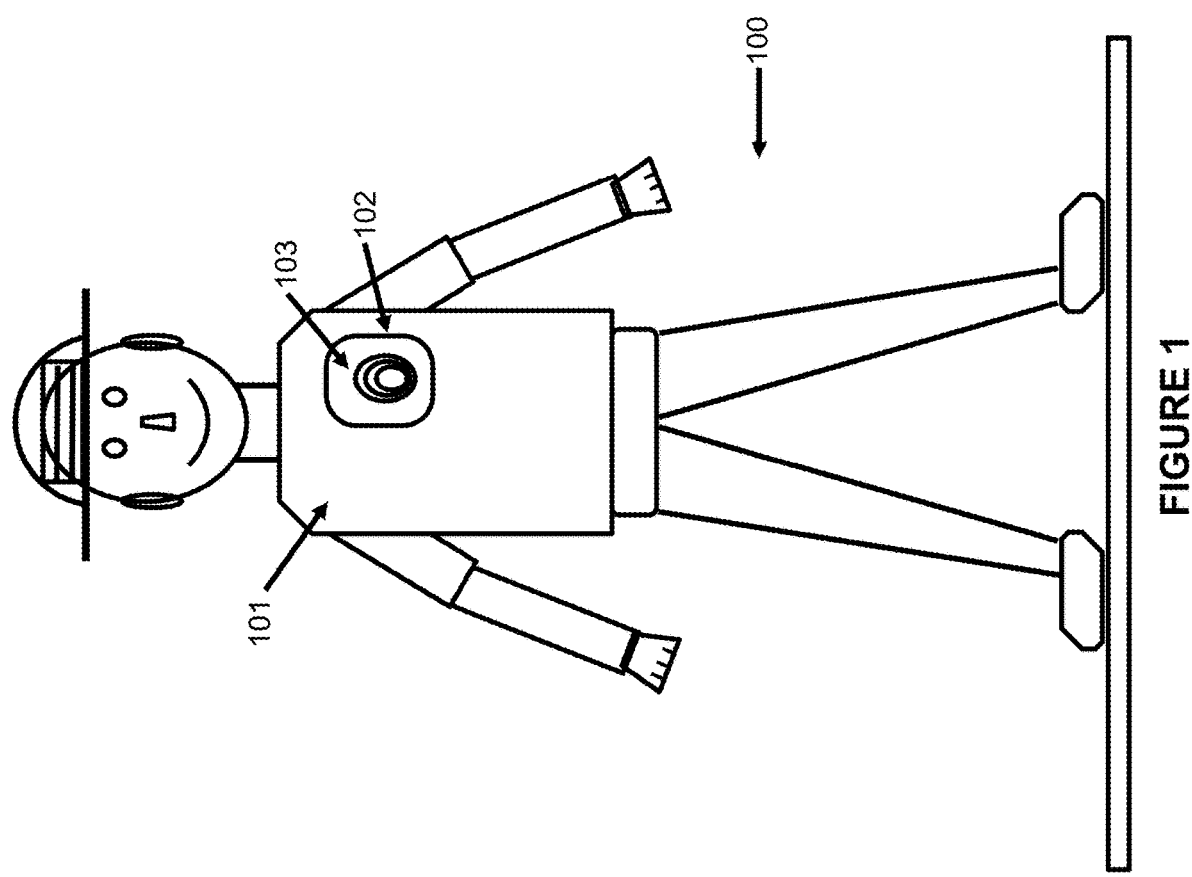
FIG. 1 shows a person wearing a small flat patch, containing bio-physical measurement devices and wireless communications equipment, attached to the outside of an upper undergarment.

FIG. 1 shows a basic wearable configuration 100. The person ("Subject") is wearing an undergarment 101, with a thin, low power electronic "patch" assembly 102 that includes a high Q flat coil inductor 103. Assembly 102 is smaller than the one shown in the figure. Not shown in the figure are any over-garments that cover the undergarment 101 and assembly 102, allowing the latter to be comfortable and unobtrusive. Inductor 103 is part of a tuned circuit probe that is in turn part of an eddy current measuring circuit.

In addition to an eddy current measuring device, assembly 102 could contain a variety of sensors and signal processing circuits. It could continuously measure heart rate, respiration rate, and other biophysical variables and communicate this data to a smart phone worn by the subject or to some other assembly close to the Subject, either of which could, in turn, send the data anywhere, including a hospital or ambulance station.

The inductor 103 of the probe is excited with an AC current, and emits an AC magnetic field that reaches the target, in this case bodily tissues, inducing AC currents in them. The component of this induction current that is in phase with the current in the probe in turn creates its own magnetic field that reaches back to the probe to induce a voltage of the opposite phase as the original excitation voltage. It therefore produces an effect equivalent to adding a series resistance to the inductor, lowering its Q. Thus, if the inductor exists within a parallel tuned circuit that is excited with AC at its resonant frequency and the AC current in the target is in phase with that of the probe, its resonant frequency is not changed, but the line voltage and resistance is decreased. The component of AC current induced in the target that is in quadrature phase with the current in the probe is reflected back to the probe to produce an effect equivalent to adding a series reactance to the inductor. Thus, if the inductor exists within a parallel tuned circuit and the AC current in the target is in quadrature phase with that of the probe, its resonant frequency is changed, but the line resistance at the new resonant frequency is not decreased. If the AC current in the target is at some intermediate phase angle with respect to that of the probe, there is a combination of reduced Q and shifted resonant frequency.

The scientific journal "Sensors" (2014, Vol. 14, 1039-1056 includes an article by Teichmann et. al. detailing an experimental eddy current system to measure heart and respiration rate. The authors do not discuss or report on measurements made of the Q of an inductor or parallel tuned circuit, or line impedance of same. They report only on apparatus that includes a probe inductor and capacitor placed within a Colpitts Oscillator circuit and measurements of said oscillator frequency variations to measure changes within the human body to obtain pulse and respiration rate data. Eddy currents in the body have only a small phase component orthogonal to the inducing currents in the probe tuned circuit; as the tissues are mainly resistive. Therefore, the authors needed to inject a relatively large circulating current into the tuned circuit to measure the small oscillator frequency variations in a timely fashion and with sufficient signal to noise ratio. They also needed multiple probe sites to obtain the necessary data quality. Total power drain is 620 mWatt, which is not at all conducive to the commercial goals listed in the instant patent.

In contrast to the above publicly disclosed system, the solutions pursuant to the invention detail in the instant patent measure the predominant in-phase reflected impedance component, use only a single probe, and consume only about 33 mWatts.

Figure 2:
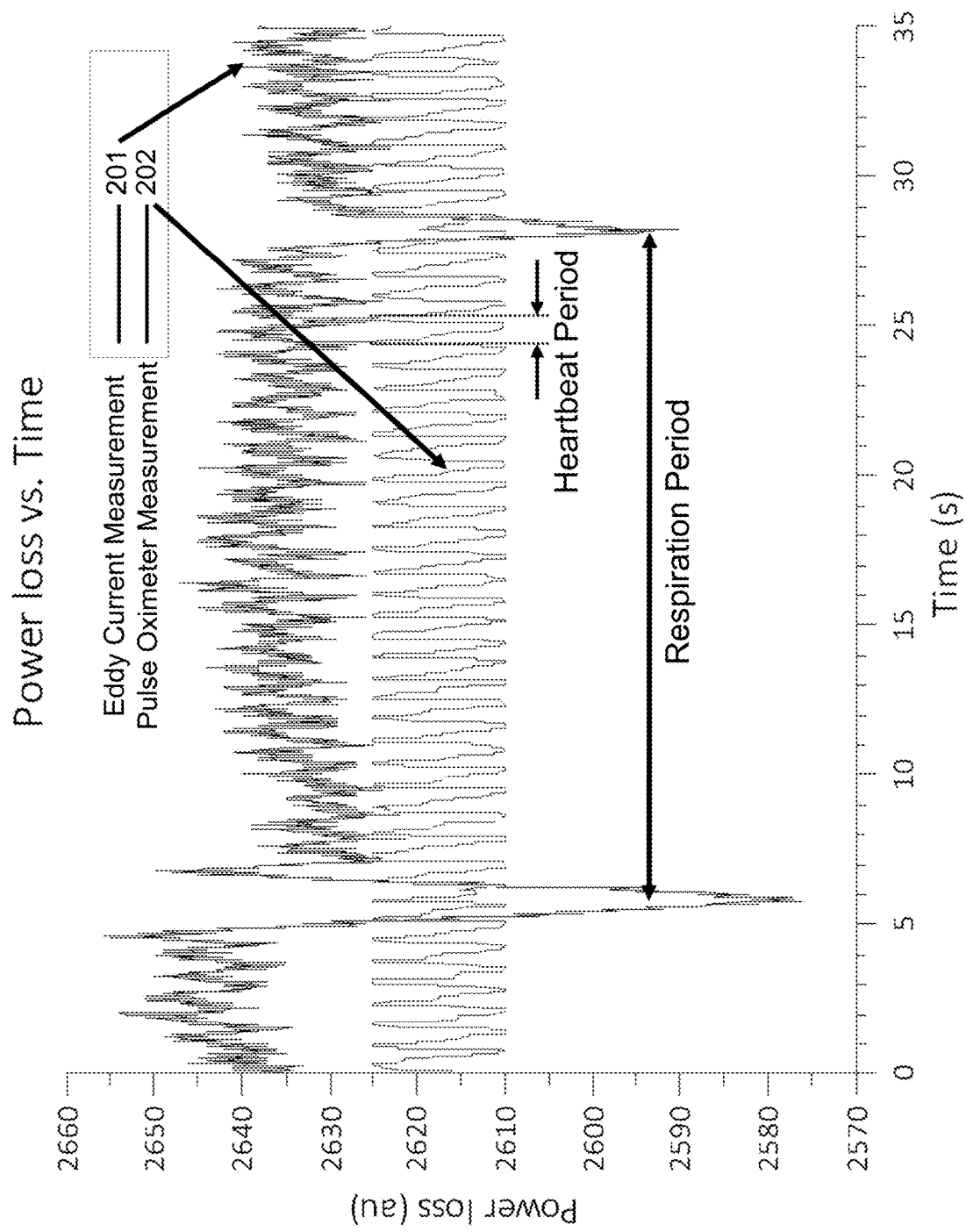
FIG. 2 shows heart rate and respiration rate data, examples of bio-physical measurements resulting from the apparatus represented in FIG. 1.

FIG. 2 shows data obtained by the inventors using apparatus pictured in FIG. 1 and described in one of the embodiments. The vertical, "power loss" scale shows relative units of power lost in the inductor 103. The upper trace 201 is the eddy current data showing heart and respiration rate. The lower trace 202 does not belong on this graph but is shown superimposed for comparison. Trace 202 is heart beat data from a pulse oximeter. The data shown is prior to filtering. Respiration and heartbeat (pulse) period are clearly shown from the eddy current measurement.

Figure 3:
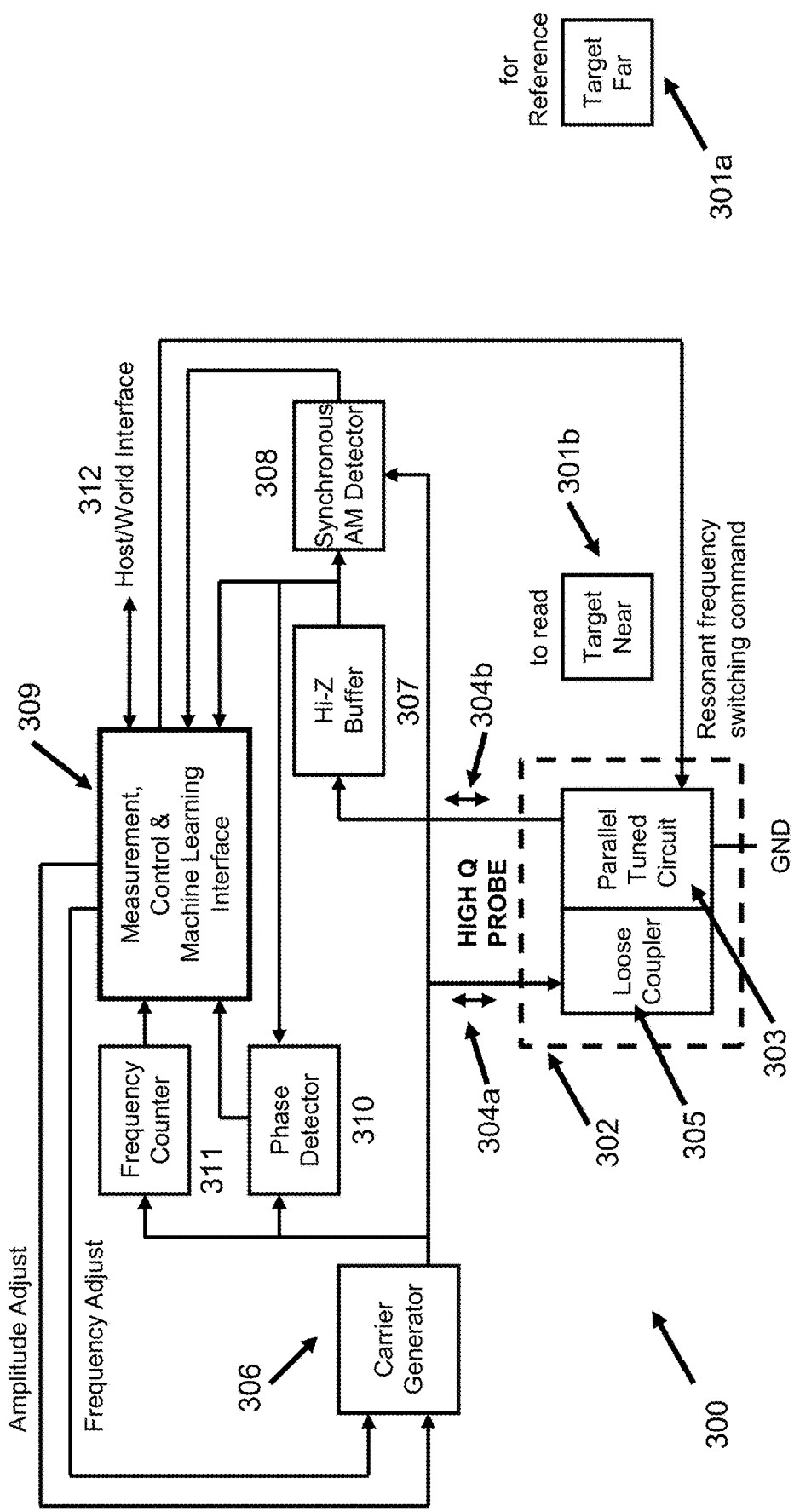
FIG. 3 shows an example system architecture of an instrument to measure eddy currents using a frequency agile monochromatic signal source and passive tuned circuit containing a coil inductor.

FIG. 3 shows an instrument system design to measure the dimensions, conductivity, distance, direction, and other properties of an object, called "Target" 301, by detecting eddy currents in it that are induced by a magnetic probe assembly, 302, and reflected back by it to said probe. Target 301 could be any object that is not an electrical insulator, such as a metallic machine part or a human heart. An AC current, created within probe assembly 302 produces an AC magnetic field that induces currents in any nearby objects that also conduct electricity. The induced current produces its own magnetic field, which in turn induces currents at the location of the original currents. This latter current can have the correct polarity to partially cancel out the original current. Thus, by monitoring the original AC current one can infer the proximity magnitude and physical characteristics of objects that conduct electricity.

When designing a probe assembly it is useful to create as large a magnetic field as possible for the amount of power supplied to it, especially in the expected direction of an object to be measured. One such method is to build a conducting component in the configuration of a "coil", which could be helical, flat, flat spiral or a combination. A coil is one form of "inductor". It is equally useful to design the probe assembly such that it consumes minimum power. It is further useful that the current within the inductor changes as much as possible when the Target is moved relative to the probe.

The above goals are facilitated by placing the inductor in a parallel tuned circuit 303, where the frequency of the applied AC power is at resonance. For a parallel tuned circuit at resonance, the circulating AC current around the inductor and capacitor can be very large whereas the AC currents that transfer energy to and from the tuned circuit, called "line" currents 304, can be very small. If the losses by a parallel tuned circuit at its resonant frequency are small, the circulating current and line voltage could be very high, and the line impedance is resistive and could be very high. Moreover, these conditions exist over a very narrow percentage frequency range. The ratio of instantaneous power circulating between the inductive and capacitive elements and the power being dissipated from these reactive elements by losses is defined as Quality Factor ("Q").

There are at least four sources of loss that can reduce the Q of tuned circuits. If it is not connected to other circuitry and isolated from all conducting objects, Q is reduced by usually unintended losses of the reactive elements. At the frequencies of interest for the instant disclosure, almost all of these losses are in the inductor, such as from effective resistance of the wire used in its construction. This resistance ("Rs"), and all other types of tuned circuit loss, can be modeled by inserting a small resistance in series with the inductor or by a large resistance ("Rp") in parallel with the inductor and capacitor. The Q value for this totally isolated configuration, is termed "unloaded Q", and the Q value for all other types of loss is termed "loaded Q".

If the tuned circuit is connected to other circuitry, such as for driving it with a signal or extracting a signal, if there are finite resistance values associated with the connection, the tuned circuit is "loaded down", delivering some of its power. A third type of loss is electromagnetic radiation, whereby power is lost to space and never returns. This type of loss is negligible in apparatus pursuant to the instant disclosure, owing to configuration dimensions being minuscule compared with wavelength.

A fourth type of loss, eddy current loss, is the subject of the instant patent. Unlike the other types of loss, it does not occur within the tuned circuit 303 itself or within connected circuitry, but rather within the surrounding conducting objects, including target 301b, having eddy currents induced by the magnetic field of the tuned circuit inductor. The magnetic fields created by the eddy currents impinge upon the tuned circuit inductor to decrease its field strength and circulating current as if there were losses in the tuned circuit, but there are no losses in addition to those that already exist when the external conducting objects are not present.

There has been much work over the years to minimize inductor losses. For instance, inductor coils are sometimes constructed with wire consisting of many separately insulated strands in order to maximize surface area; as, for frequencies several hundred kilohertz and above, virtually all current is confined to the surfaces of conductors. There are additional methods to increase unloaded Q, such as by employing core material within the coil or even "resonator" components that are not coils at all. These methods are often suitable when the purpose for high Q is to implement a solely circuital function, such as a low noise oscillator or highly selective filter. The instant patent however, involves building a probe, which by its very nature requires the magnetic field to exist in space, whereas the inductors or other resonators mentioned above restrict the magnetic field to within the inductor structure or produce no magnetic field at all.

If the circuitry that transfers energy to and from the tuned circuit is loosely coupled 305 to it, the high unloaded Q becomes a relatively "high loaded Q" that is not very much lower than the unloaded Q. Under these conditions, a large circulating current, which produces a large magnetic field and small line current, which translates to very high line impedance and very high AC line voltage, do occur. Such conditions permit maximum line voltage reduction when a target 301a is moved nearby 301b.

In FIG. 3, the Carrier Generator 306 frequency could be swept to find the maximum AC voltage at the Hi Impedance Buffer 307, using the Synchronous AM Detector 308. Alternatively, detector 308 could be used to measure the voltage at a given frequency that is close to resonance, but it is important to keep tuned circuit 303 at resonance for minimum power drain. As another alternative, tuned circuit 303 could be maintained at resonance by using it as the resonator in an oscillator circuit. There are certain oscillator circuits that load the tuned circuit very lightly, which maximizes loaded Q of the resonator and the AC voltage across it.

Carrier Generator 306 may have a low impedance output; so it must drive parallel tuned circuit 303 through a Loose Coupler 305 in order to maintain high loaded Q. This can take the form of feeding the inductor through a tap or splitting the resonating capacitor into two series components and feeding between them. The high loaded Q of the parallel tuned circuit is also preserved by the high impedance input buffer 307, "Hi-Z Buffer". Thus, AC line voltage and other aspects of the signal existing within the parallel tuned circuit 303 can be measured with minimal degradation of its loaded Q.

If the Target 301a is far enough away and/or conducts electricity poorly enough (termed the "Reference" condition), the parallel tuned circuit is maximally isolated and therefore maintains its high loaded Q. Such circuits have the following characteristics: At resonance, probe 302 output line impedance value is very high. Probe 302 output line voltage is very high and the line current 304b is extremely low. In addition, the output line voltage is very close in phase to that of Carrier Generator 306 output. Moreover, if the carrier generator frequency is varied a small amount either above or below the resonant frequency, the output line voltage drops very rapidly. The value of this output line voltage at the carrier generator 306 frequency for which it is maximized is one measurement under reference conditions that can be compared with measurements that include eddy current effects from a target 301b.

Inasmuch as Carrier Generator 306 needs to be varied in frequency to reach the tuned circuit's 303 resonant point, measurement of probe 302 output line voltage 304b could be used for that purpose. Using this method has the disadvantage that this output line voltage drops on either side of the resonant frequency; so it does not indicate whether to slew the generator frequency up or down without moving it in one direction or another as a test (called "hunting"). Alternatively, the carrier generator 306 frequency could be swept until its output voltage and probe 302 output line voltage are in phase. This zero-phase condition is easily reached and maintained; as the phase difference polarity depends upon whether the generator frequency is above or below the tuned circuit resonant frequency. Moreover, the phase change is considerably abrupt under high Q conditions for which the output voltage peak is narrow, which assists maintaining resonance accurately. Under low Q conditions, the phase change is not so abrupt, and zero phase difference does not coincide with the output voltage vs. frequency peak. However, at low Q, this peak is relatively broad, and the percentage difference between the voltages at peak and at zero phase difference is negligible.

Once the Probe 302 parallel tuned circuit 303 is processing a carrier signal at resonance, the no-target reference condition can be measured for later comparison when there is a nearby target 301b producing eddy currents. The basic parameter is Q. A standard Q value measurement is to vary the generator 306 frequency above and below the resonant frequency and record the frequencies for which the probe output voltage drops by 3 decibels. The resonant frequency divided by the difference of the 3 dB frequencies is by definition the Q value. Any additional loading of the tuned circuit, such as by effects of a target 301b, lowers the Q, causing this 3 dB frequency difference to increase. Thus, Q value can be used as a scale for all eddy current measurements.

Measuring Q value directly could be supplemented or substituted by also measuring the probe 302 output line voltage 304b, which is also an indicator of Q value. Comparing this voltage reading under reference conditions can be made with those obtained with the presence of targets, as long as the carrier generator output voltage is kept constant or taken into account.

In summary, any additional losses to tuned circuit 303—such as adding resistance in series with the inductor, lowering the Buffer input resistance, or by moving a target close enough to the probe, lowers the loaded Q of the parallel tuned circuit, causing its line parameters such as probe output voltage to change.

In some instances, it is important to select the tuned circuit's 303 resonant frequency, such as for regulating sensitivity to depth of a target within a container or biological entity. This could be accomplished by varying tuned circuit 303 capacitor value using variable components, switching, or both. Further, in some instances, it is important to adjust the power output from the Carrier Generator to obtain the optimum circulating current within the probe tuned circuit 303. For instance, after carrier generator 306 frequency is adjusted for maximum eddy current sensitivity of a given target at a given depth, it may be possible to reduce carrier generator 306 output power to minimize AC power in the target and DC power drain.

Specifically, FIG. 3 contains a magnetic probe 302 that includes a very high Q parallel tuned circuit 303 with an inductor that is designed to distribute a magnetic field through space. The probe 302 also contains necessary resonating capacitors and switching means to resonate at a variety of frequencies. Also in this probe 302 is a means to couple loosely into, 305, and out of the tuned circuit, in order to obtain a very high loaded Q. The Probe Parallel Tuned Circuit Output line 304b drives only a very high input impedance buffer 307, whose main function is to maintain the high Q of the Probe tuned circuit 303.

The Buffer 307 drives the Measurement and Control Module 309, a phase detector 310, and Synchronous AM detector 308, which provides a varying DC voltage to the Measurement and Control module 309 that represents the AC amplitude level at 304b. This detector 308 is automatically synchronized by the same carrier signal that is used for the signal being measured; so no frequency locking is required. Only at tuned circuit 303 resonance will accurate amplitude measurements be made, and under these conditions, Carrier Generator 306 and Probe 302 line output 304b are in phase, the condition needed for synchronous AM demodulation. Unlike detectors using diode rectification, the synchronous AM detector is very low noise and has a very large linear range. Nevertheless, AM detectors other than synchronous types could be used.

In order to service many applications envisioned by the instant disclosure, Carrier Generator 306 can operate between roughly 2 MHz and 20 MHz. It operates at frequencies and output amplitudes as directed by control module 309 and delivers its signal to the probe tuned circuit input line 304a, phase detector 310, frequency counter 311, and Synchronous AM Detector 308. Probe input line 304a needs varying amplitude, and the other blocks are relatively insensitive to amplitude.

The Measurement, Control and Machine Learning module 309 receives the demodulated probe output line 304b signal from Synchronous AM Detector 308 in order to monitor the Probe parallel tuned circuit 303 output AC voltage level 304b while it is at resonance. It also receives the buffered 307 Probe line output 304b signal directly in order to measure amplitude using its internal asynchronous AM detector, when such measurements must be made while said tuned circuit is not at resonance. It also receives the output of phase detector 310 to measure the phase angle between probe output line 304b and Carrier Generator 306 output. It controls and monitors the Carrier Generator's frequency and controls its output amplitude. It could use this control capability and information to calculate the Probe tuned circuit 303 Q in several different ways under Reference and Target Measurement 301b conditions, and it could also determine Target 301b resistance linearity. It also reads carrier generator 306 frequency using Frequency Counter 311. It also operates capacitor switches and other means in the probe assembly 302 to vary the resonant frequency. It interprets the Q values in accordance with directions from the Host 312 as to Target 301b physical properties and/or separation. Finally, it communicates with neighboring equipment, such as computers and cellular phones in order to receive commands, report out data, and benefit from high speed calculations, such as those needed for machine learning.

Certain properties of target 301b can be identified by the phase angle of the eddy current in the target relative to that in the probe inductor 303 as well eddy current loss effects captured by probe inductor 303 loaded Q variations. Phase angle information can be derived by also monitoring the tuned circuit's 303 resonant frequency in the presence of target 301b as compared with when this target is absent. Frequency counter 311 could be used to measure exact frequency shifts of carrier generator 306 that are needed to track probe 302 resonant frequency shifts caused by targets having induced currents that are not in the same phase as the incident magnetic field from the probe.

Any property of a target 301b that reduces the Q relative to reference conditions of the probe's tuned circuit 303 can be measured if the property can be isolated from all other properties and conditions that reduce Q. For instance, if a conductive sphere located in the axis of the probe tuned circuit inductor is moved radially closer to and further away from the probe, the separation can be tracked; as there are no other changes that can affect the measurement. On the other hand, if any velocity vector component is not radial, the motion will cause the sphere to enter regions that are off axis, with differing sensitivity. Even if the object stays on the axis but is a disk instead of a sphere, angular position of the disk is mixed in with separation and must be isolated.

If a probe is held at a controlled distance from a container of stationary liquid or a container of liquid in motion such as a pipe, which could be underground, properties that affect conductivity can be detected and monitored. However, it is essential that only one conductivity-affecting property is changing and that a reference reading is made with that desired property at a known concentration. A probe can also detect the presence or absence of a conductive liquid or other substance, such as in diaper wetness or bladder fill level instruments. Tank liquid level has been monitored for many years, but use of a probe of this type may be a lower cost or safer alternative.

Another controlled variable is oscillatory motion of an object. Concentrating only on oscillatory repetition rate and eddy current as a function of time within each oscillation cycle has a tendency to be isolated from all other properties of the target. Thus, heart rate, certain aspects of its motion, and respiration rate can be measured, which are major applications of this patent, as opposed to certain metallic target position industrial applications well covered in prior art.

Figure 4:
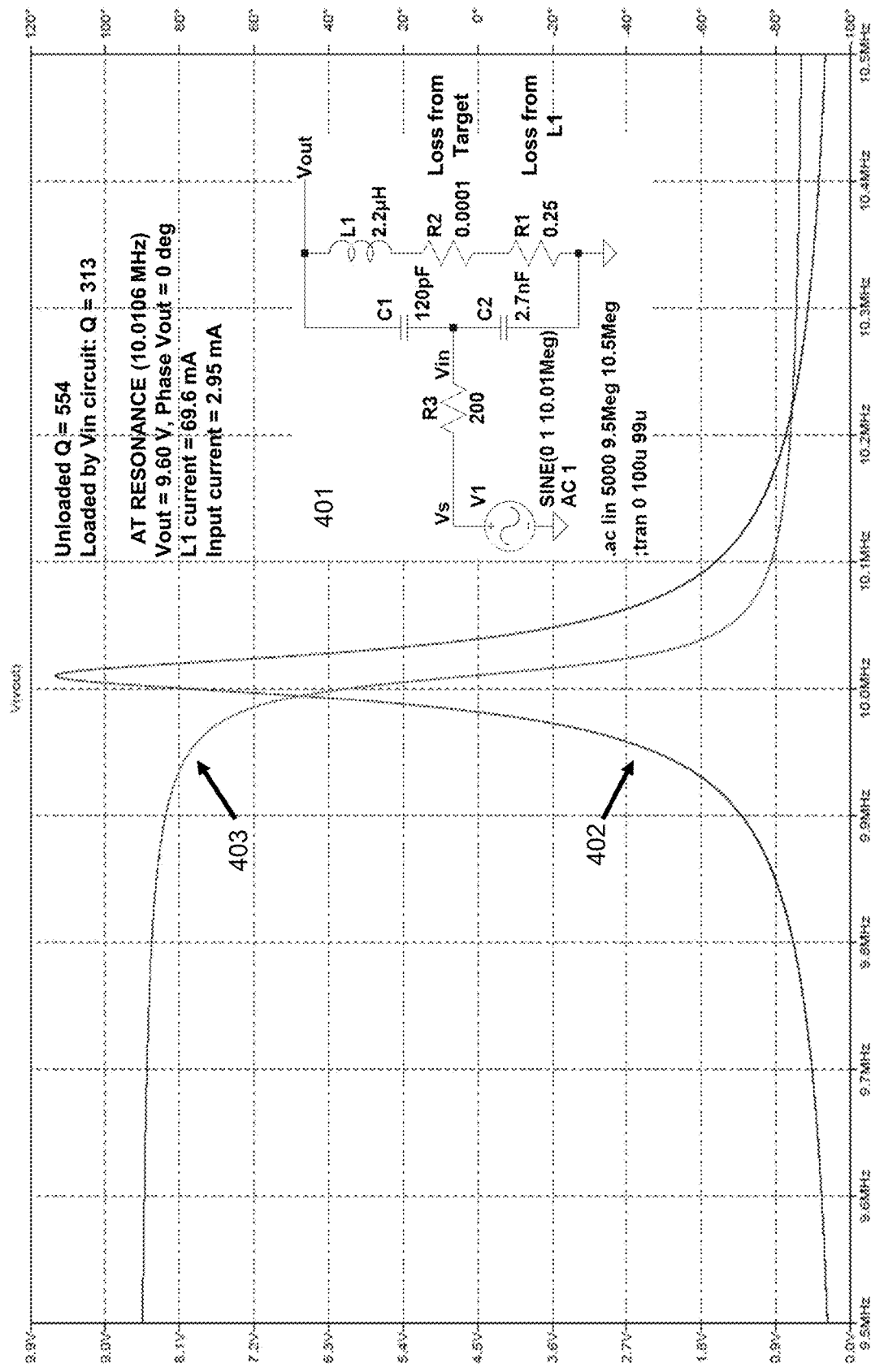
FIG. 4 shows the frequency and phase response near resonance of a high Q parallel tuned circuit containing a coil inductor that is not in proximity of objects that produce eddy currents.

FIG. 4 shows a simulation of a practical probe circuit example that is well suited to eddy current measurements of all loss amounts but especially for application where there are small losses, such as from targets that are small, far away, low conductivity, or buried in lossy material.

The parallel tuned circuit 401 consists of five components. L1 is a 2.2 uH inductor that is designed to distribute its magnetic field into space and to have a high Q. The two capacitors, series connected 120 pF and 2.7 nF, resonate this inductor to 10.0106 MHz. R1 represents the inductor losses by an effective resistance of 0.25 Ohms. R2 represents losses within the eddy current target, which is absent for this example so is shown as nominally 0 Ohms.

When R3 is disconnected, the tuned circuit is completely isolated, as it is assumed that Vout is connected to an infinite impedance buffer. Its unloaded Q is 554. The ratio of C1 and C2 and values of R3 and V1 are chosen minimize loading of the tuned circuit but still permit relatively large signals to measure and average power drain under 10 mWatts under all conditions. By lowering V1 (Vs), the power drain drops more quickly than signal levels. This input circuitry lowers the Q to 313, as can be determined by the simulation. If the input circuit, including R3, were removed, the Q would be lowered to 313 by inserting a 0.18 Ohm resistor, R0, in series with R1 and R2.

Using the simulation, this loaded Q was determined by the elementary "3 dB down" method on the amplitude response curve 402, as described in a previous paragraph. It was also determined that Vout would be 9.60V, and the current through L1 is 69.6 mA, even though the input current is less than 3 mA. Of course, the input current rises rapidly if V1 frequency, shown on the graph horizontal axis, differs from resonance.

The phase curve 403 shows, as expected, that the phase difference between Vout and Vs is 0 degrees at the resonant frequency (as measured by the amplitude peak). It also shows a rapid change from leading to lagging below and above resonance, which can be used as explained in a previous paragraph, to easily find and hold the resonant frequency.

Figure 5:
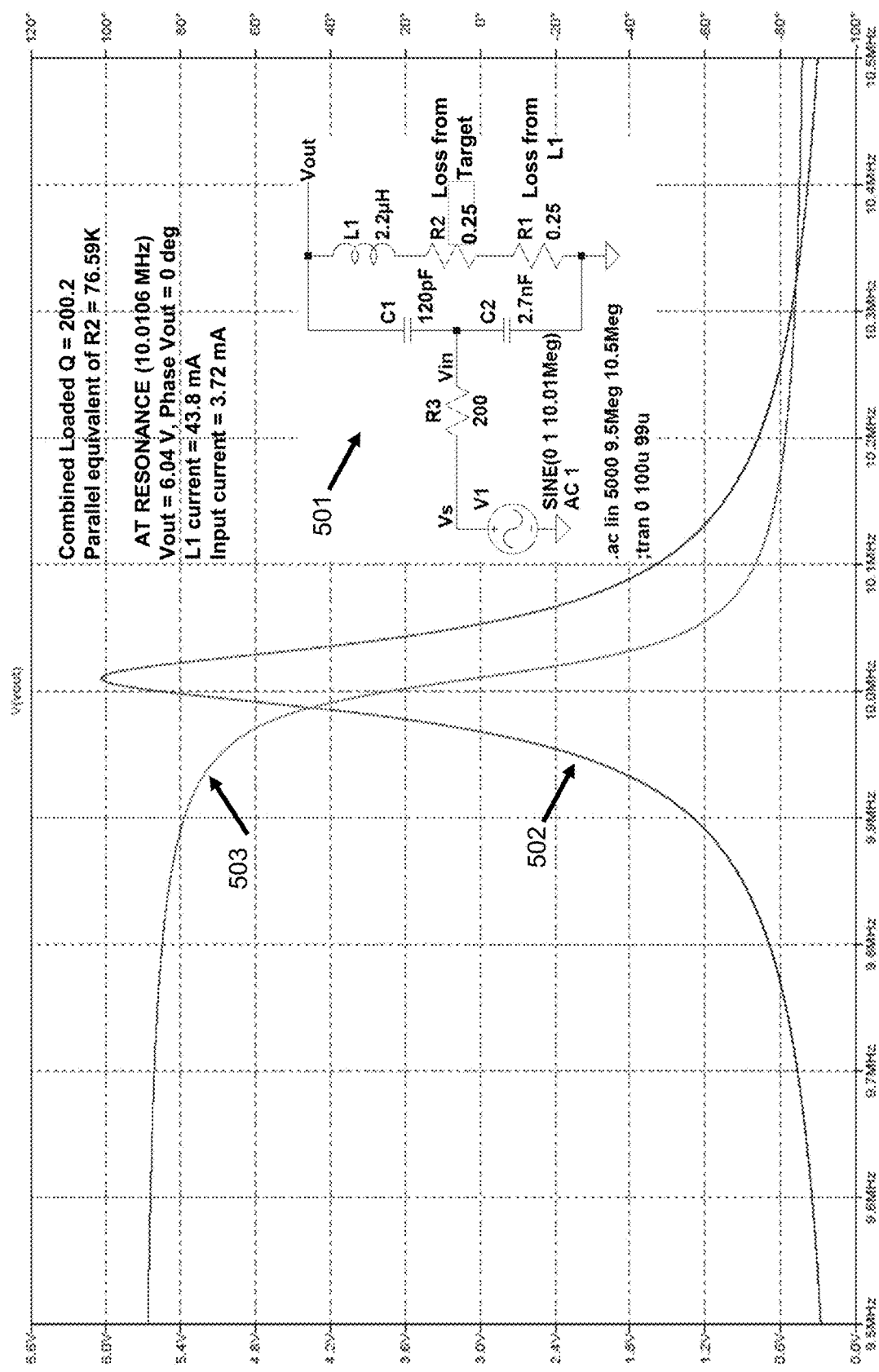
FIG. 5 shows a configuration identical to that of FIG. 4, including the frequency and phase response near resonance of a high Q parallel tuned circuit containing a coil inductor but also a series resistance that simulates the proximity of objects that produce small eddy current losses.

FIG. 5 shows the same conditions as FIG. 4, except for the effects of a target. This is shown by R2 as 0.25 Ohms instead of 0 Ohms. The target is small enough that its loss contributes only an equal amount of a Q=554 inductor. "Small" target as defined here means that it has some combination of low conductivity, small size, and large separation from the probe. The same loss could be depicted by a circuit with R2=0 (again), but a resistance of 76.59K going from Vout to ground. This is the so-call "parallel equivalent" resistance.

The loaded Q has dropped all the way to 200.2, as measured by the standard 3 dB down method, but an easier measurement is that Vout has dropped all the way from 9.60 to 6.04V. The phase shift is still very close enough to zero, to clearly indicate the narrow voltage peak. L1 current has dropped from 69.6 to 43.8 mA, which has a special significance. It should be noted that the Vout ratio=L1 current ratio, =9.60/6.04=69.6/43.8=1.59.

The fact that L1 current diminishes with target loss is an elementary part of this measurement process. The fact that L1 current is permitted to diminish with target loss indicates that magnetic flux density (which is directly proportional to L1 current) is not standardized within the eddy current measurement region. If, for instance, a given target material has an increasing conductivity, its eddy current loss will increase proportionally, causing it to be probed with a smaller flux density (and rate of change of flux density). If the conductivity does not vary with flux density, there may be no effect upon the measurement, which is normally the case for eddy current measurements that do not penetrate a surface.

However, there are situations for which it is important to maintain constant flux density for all measurements, even where the target conductivity does not vary with current density. Certain particular measurements that are the main subject of the instant disclosure involve targets that are located within media, including but not limited to human tissue. The depth penetration of eddy currents depends upon frequency and magnetic flux density. The frequency is easily maintained to be essentially constant, but the flux density in the region of interest must be kept constant as well; so the probe inductor current must be kept constant for all measurements.

Figure 6:
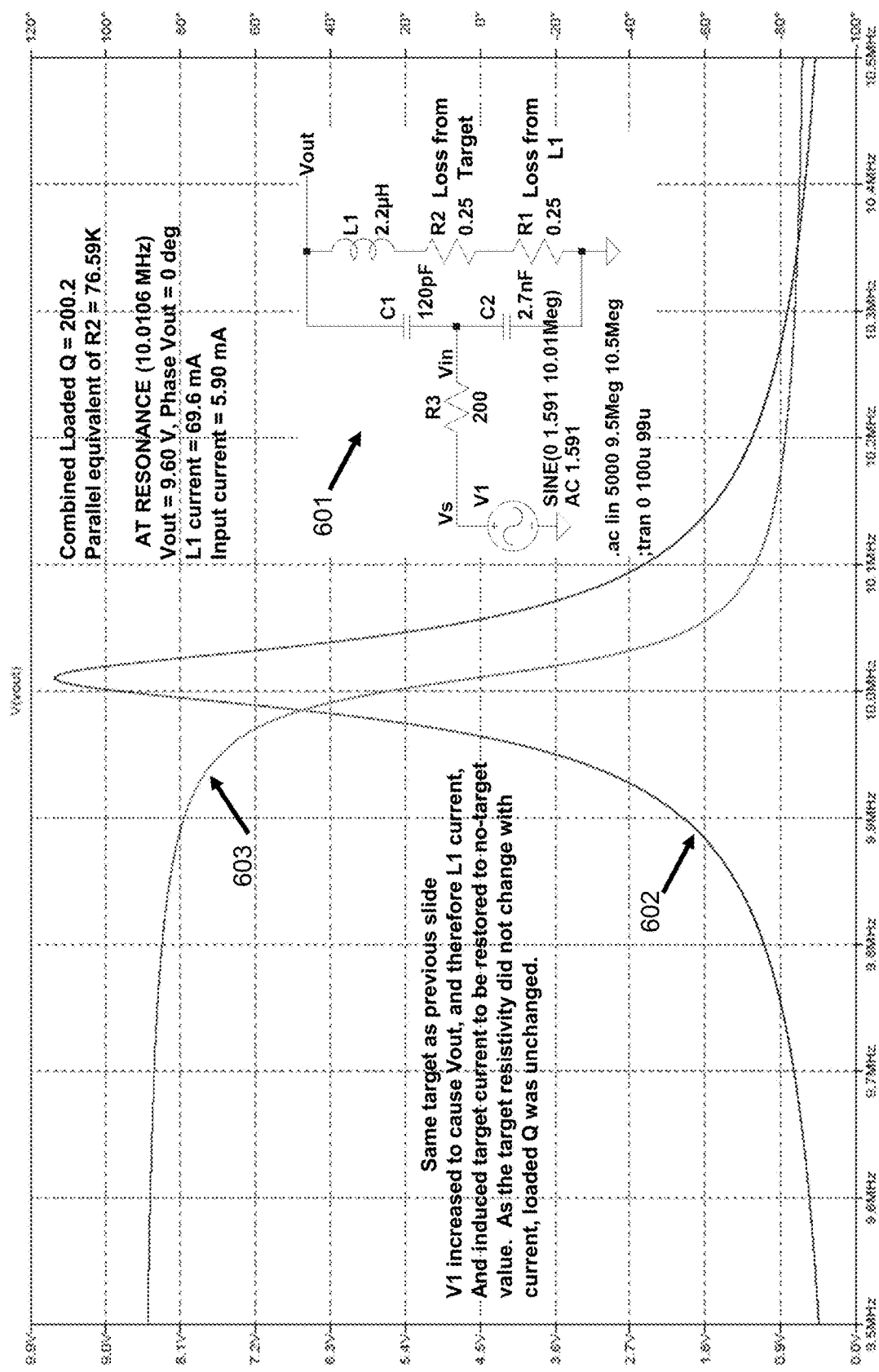
FIG. 6 shows the frequency and phase response near resonance of a configuration identical to that of FIG. 5, except that the tuned circuit input level from the signal source has been increased to obtain the same tuned circuit output level as that obtained in FIG. 4.

Therefore, FIG. 6 shows the same circuit conditions as the previous slide, except that Vs has been increased from 1V to 1.591V, an increase by the same ratio as the decrease of Vout between the previous slide and the second previous slide. The result is that the Vout and L1 current have been restored to their no-target reference values, whereas the simulated Q is showing the effect of eddy current loss as represented by R2 still being 0.25 Ohms instead of 0 Ohms. Of course, R2 did not change in value, with increased circulating current, but if a real target has conductivity that varies with flux density, the Q measurement would not come out the same for different excitation voltages Vs, and the non-linearity curve could be measured by this instrument.

Referring again to FIG. 3, a formal procedure, which could be orchestrated by the Measurement and Control Module 309, is needed to implement automatic constant Probe tuned circuit inductor current. First, a suitable frequency within, say, the 2 to 20 MHz range is selected for the particular target configuration and measurement goal, and the Probe parallel tuned circuit 303 is chosen or adjusted to match. Then, a particular Vout value, representing a particular Probe inductor (L1) current, is chosen to achieve satisfactory penetration of a medium, where applicable. For some situations, this inductor current level is chosen to be only as high as necessary for the measurement, in order to draw minimum battery power. Moreover, for instruments specified to measure eddy current losses within current density and power dissipation sensitive media—especially humans—the carrier generator output voltage could be limited by ultra-reliable methods in order to achieve intrinsic safety.

The Carrier Generator 306 output value is set by "Amplitude Adjust" from Control Module 309 to a nominal level, and the frequency setting loop sets carrier generator 306 to the tuned circuit's 303 resonant frequency, as measured by zero degree phase shift between Carrier Generator output and tuned circuit buffer 307 output. Then, the carrier generator 306 level output is adjusted, as measured by AM detector 308 and digital volt meter contained in the measurement block 309 to obtain the desired FIG. 6 Vout value. These two control systems have minimal interaction and operate simultaneously; as the phase-nulling frequency setting is independent of Vout level. The Total Loaded Q is then measured by freezing the carrier generator output level but offsetting its frequency by any nominal and measured amount, say about 400 parts/million. Measuring Vout at that frequency immediately determines the Q value, using the two frequencies and two Vout levels. It is not necessary to measure the Q by its classical "3 dB down" definition; as it is mathematically related to the above measurement. Finally, common formulas or general methods covered later in the instant patent are used to derive eddy current losses within the target.

In addition to the above measurement process being automated, the preliminary operating frequency selection and Probe inductor current can also be automated under the direction of Measurement and Control module 309 to obtain reliable measurement amplitudes at minimum necessary battery power and/or eddy current dissipation levels.

It can also be shown that if Vs is controlled to keep Vout at some reference level (in the instant disclosure 9.60 Volts), which keeps L1 current at a constant level, once a direct Q measurement is made, all further measurements can be made without a direct re-measurement of Q. It is only necessary to use the ratio of Vs value for any new measurement to that obtained at the first measurement.

For instance, using examples elsewhere in the instant disclosure, if a Vout value of 9.588 is chosen to obtain L1 current of 69.3 mA in order to obtain the desired sample penetration depth, it may happen that Vs=1 Volt is needed when there is no target. The measured Q value as always represents R0+R1+R2, in this example 0.18, 0.25 and 0 Ohms, total 0.38 Ohms. As R0 and R1 are known constants, where R1 is represents the Ohmic loss of L1 and R0 represents the series equivalent resistance of input circuit loss, R2 is computed to be 0 Ohms. If a target represented by an R2 value of 0.25 Ohms (R2p=76.6K) is caused to be in place, the total of R0+R1+R2 becomes 0.68 Ohms, about 1.58 times larger. It can be shown that to a close approximation, the voltage Vs that is needed to maintain Vout at 9.588 volts is 1.58 times larger than that needed for the previous measurement (in this example 1.58 Volts). We then have the ratio of the second R0+R1+R2 to the first R0+R1+R2 equal to 1.58, and the only unknown is the second R2, the series resistance representing the eddy current.

Figure 7:
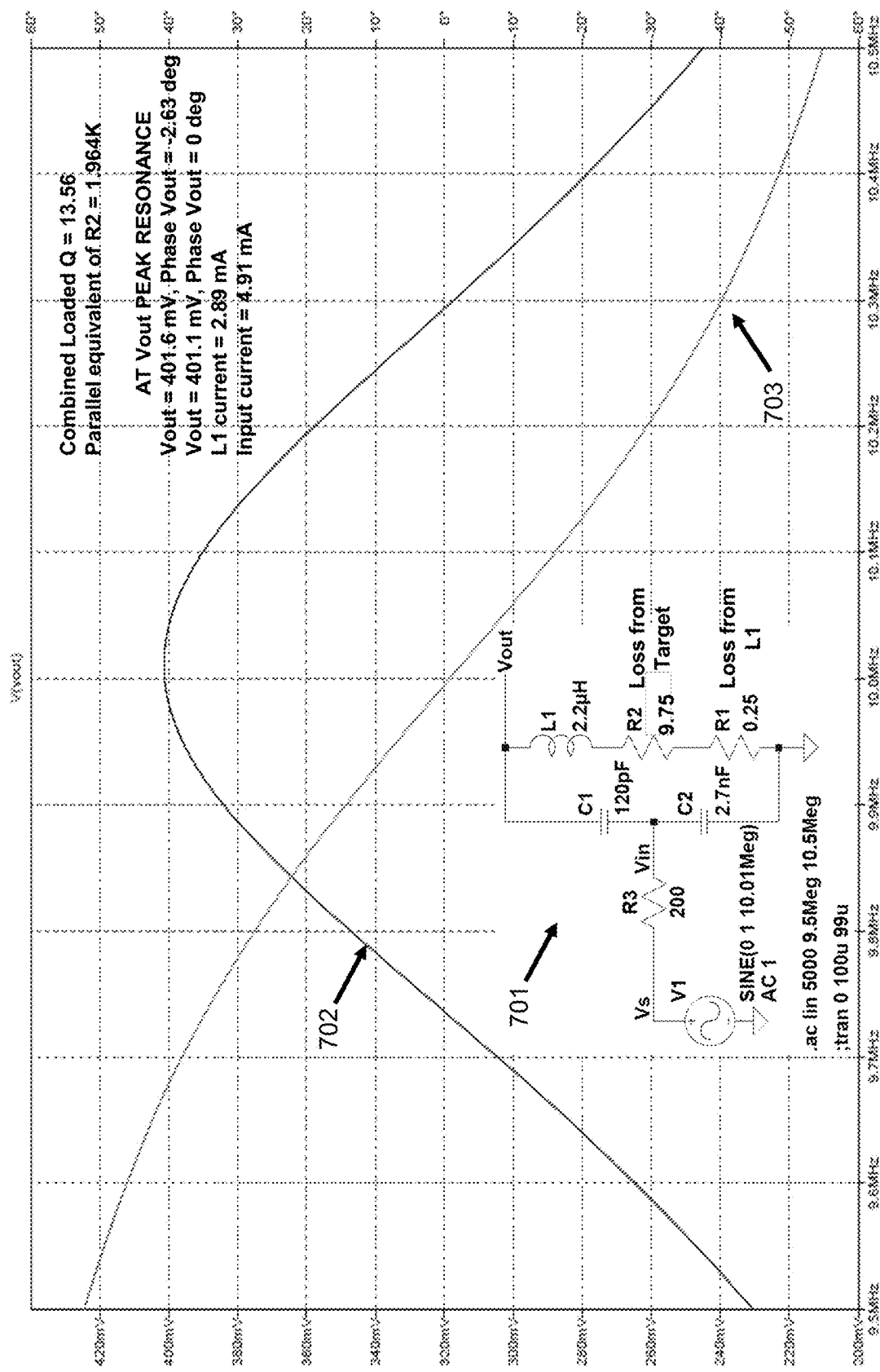
FIG. 7 shows a configuration identical to that of FIG. 4, including the frequency and phase response near resonance of a high Q parallel tuned circuit containing a coil inductor, but also a series resistance that simulates the proximity of objects that produce large eddy current losses.

FIG. 7 shows Vs back at the "standard" 1 Volt, but here the target loss is represented by 9.75 Ohms, 39 times higher than the inductor losses. Parallel equivalent resistance is less than 2K. Vout has dropped to only about 401 mV and L1 current to less than 3 mA. Loaded Q is only 13.56. Zero phase difference is not coincident with the voltage peak at resonance, but the peak is so broad that the Vout voltage error is entirely negligible.

Figure 8:
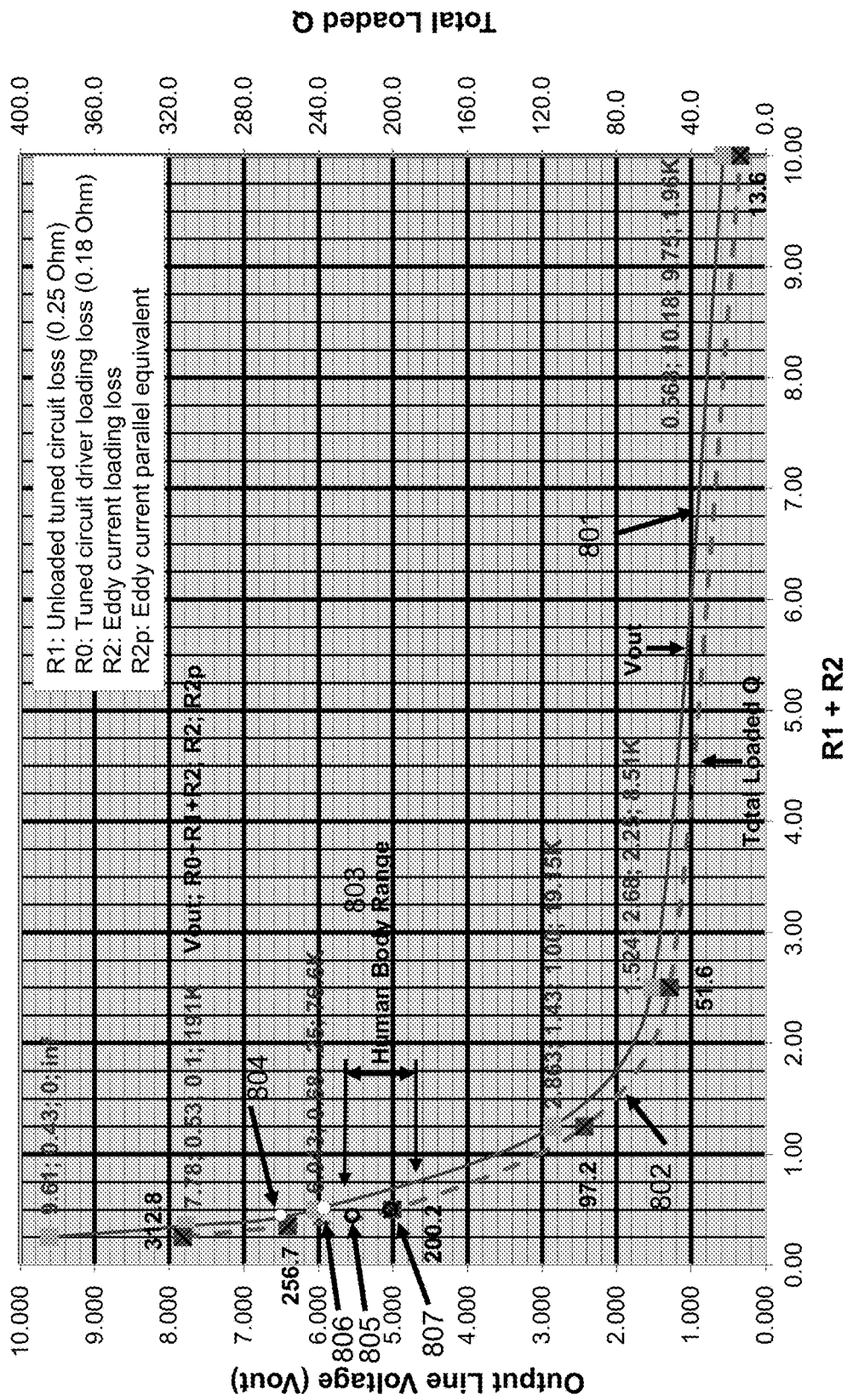
FIG. 8 shows graphs of tuned circuit Q, and output level for constant input level, as a function of totaled internal losses and eddy current losses.

FIG. 8 shows a summary of Vout 801 and total loaded Q 802 as a function of parallel tuned circuit series resistance. The Vout and Total Loaded Q curves are actually coincident; the curves were separated for clarity by choosing a total loaded Q scale that covers a wider range than the Vout scale. The Vout and Loaded Q quantities represent the total losses, but the Series Equivalent Resistance (horizontal) axis shows only R1+R2, the total of tuned circuit unloaded loss and eddy current loss. R0, the loss due to loading of the tuned circuit by the driver circuit, is omitted. Therefore, all the information is tabulated at each Vout curve data point. Each data point shows Vout, the total equivalent series resistance for all three of the loss categories (which corresponds to the total loaded Q value), the eddy current loss (R2), and the eddy current loss parallel equivalent resistance (R2p). This graph shows that the measurement method delivers a large rate of change of Vout with respect to eddy current loss, up to about 1.5 Ohms total series equivalent resistance (total loaded Q about 100. Above 1.5 Ohms series resistance, the slope becomes about 142 mV/Ohm, which still appears to be quite usable. All of these voltages scale linearly with Carrier Generator output voltage.

FIG. 8 also shows graphically what can be calculated as the final steps of the eddy current loss measurement cycle, detailed previously in the instant patent. Reviewing the variables from the schematic diagrams again, R1 is the equivalent series resistance in the tuned circuit representing losses of tuned circuit itself, with no loading. R0 is the equivalent series resistance representing losses to circuitry connected to the tuned circuit, such as the circuit that feeds power to it. X1 is reactance of L1 (and that of the total capacitance, Ct) at the tuned circuit's resonant frequency. Qt is total Q, which is measured by comparing Vout levels at the resonant frequency and a frequency close by. R2 is the equivalent series resistance representing losses to circuitry or conducting objects that are magnetically coupled to the tuned circuit, such as from eddy currents. Q2 is the Q that could be measured in the tuned circuit if it had zero internal losses and were otherwise isolated except for inducing eddy currents the conducting object. R2p is the equivalent parallel resistance (shunting the parallel tuned circuit) that in place of R2 represents the losses within the conducting object with eddy currents.

It can be shown that $Q2=X1*Qt/[X1-(R0+R1)*Qt]$. Using the constants employed in the examples of the instant disclosure, $Q2=138.388*Qt/[138.38-(0.180+0.25)*Qt]$ $=138.388*Qt/[138.38-0.43*Qt]$. It can be shown that $R2=[X1-Qt*(R0+R1]/Qt=(138.38-0.43*Qt)/Qt$. It can be shown that $R2p=[(L1/Ct)*Qt]/[X1-(R0+R1)*Qt]$ $=19148*Qt/(138.38-0.43*Qt)$. The last formula completes the process of the instrument measurement cycle, using the measured loaded Q to find the eddy current loss.

It has been experimentally verified by the inventors that when a practical flat coil inductor tuned circuit having the high unloaded Q described herein is placed at the chest of a human body, the losses from eddy currents at 10 MHz are not much more than the losses when a target is absent. As shown in FIG. 8, this "Human Body Range" 803 lies within the highest absolute value slope of the response curve. Apparently, this measurement method is especially suited to small target/low loss measurements needed for biological and other physical properties, where the target may be embedded within living tissue or other media. The key requirement is to employ a very high Q tuned circuit probe, for which a large percentage of the unloaded Q is preserved when this tuned circuit is connected to other circuitry in the instrument.

Figure 9:
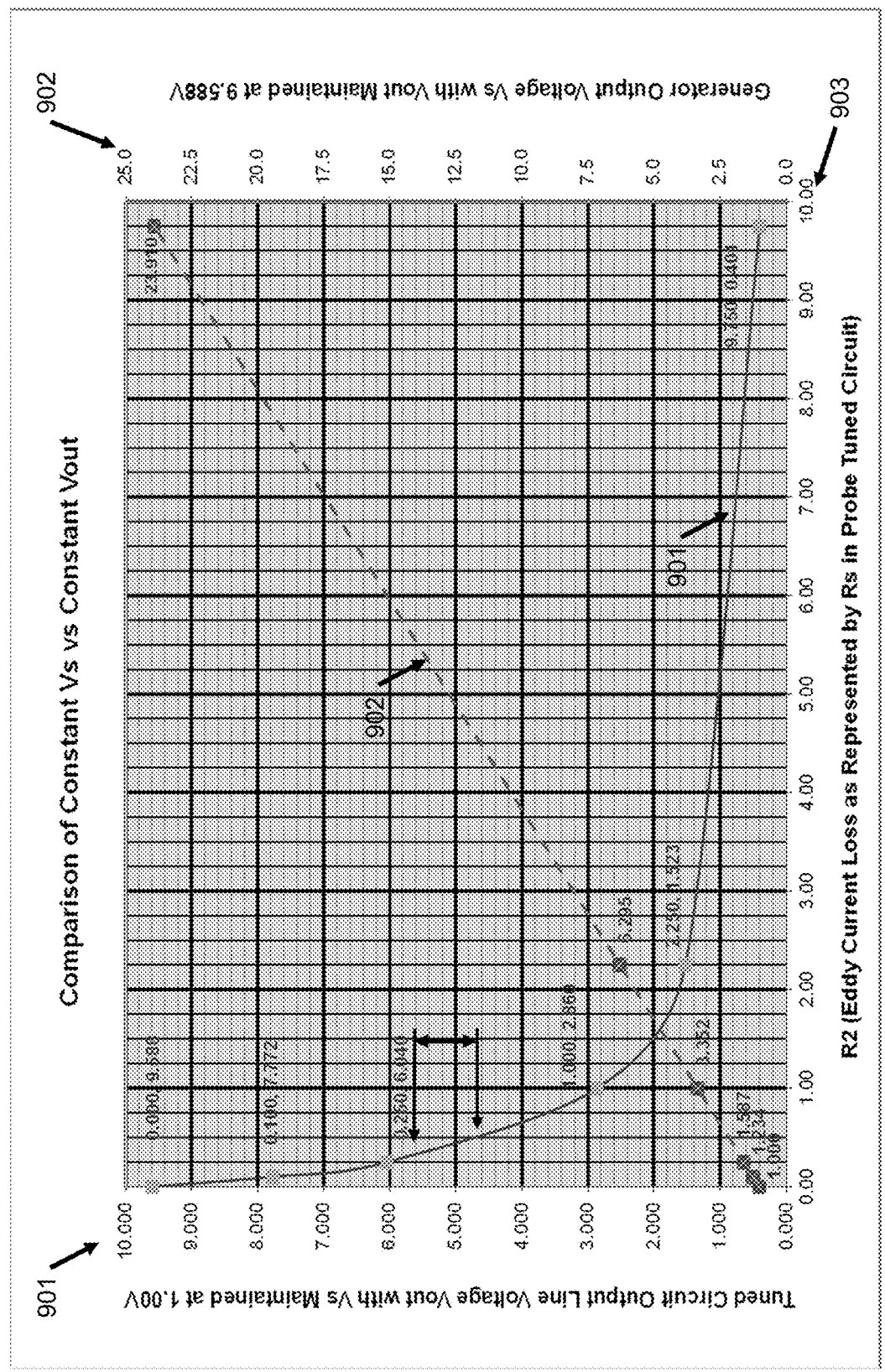
FIG. 9 shows graphs of tuned circuit output level for constant input level, and input level for constant output level, as a function of eddy current losses.

FIG. 9 shows the scale comparisons between the open, 901, and closed, 902, loop procedures. The open loop procedure keeps the carrier generator 306 voltage, Vs (for example at 1.000V) constant and allows the Probe tuned circuit output voltage 304b, Vout, and thus the inductor 303 L1 current and magnetic field, to vary. The closed loop procedure adjusts Vs to maintain a constant probe tuned circuit output 304b Vout value (for example 9.588V). For the graph 900, the abscissa 903 shows the eddy current loss alone, not combined with the constant probe inductor loss, as is the case with FIG. 8. The open loop procedure appears to be well suited for the small target measurements that are the main subject of the instant patent. For instance, as the target loss, represented by the equivalent series resistance of the tuned circuit, changes from 0.100 Ohms to 0.250 Ohms, Vout is reduced from 7.772V to 6.040V, a 1.732V difference and about a 1.29 ratio. The closed loop procedure yields a linear response. The voltage difference for these same two target losses is only 353 mV, but the ratio is identical.

The fundamental measurement description thus far has focused on the probe parallel tuned circuit 303 and has not described electrical properties of the target 301b and magnetic coupling of same to the probe 302. R2 in FIGS. 4, 5, 6, 7 represent the eddy current losses within the target. The following paragraphs and figures extend the modeling to the target itself, describe something about the magnetic field interactions, and show through rough knowledge of field distribution and human target electrical properties that the R2 values used previously may represent realistic eddy current losses. Also shown is that the eddy currents and dissipation amounts needed for accurate measurement of vital signs are well within established safety limits.

Figure 10:
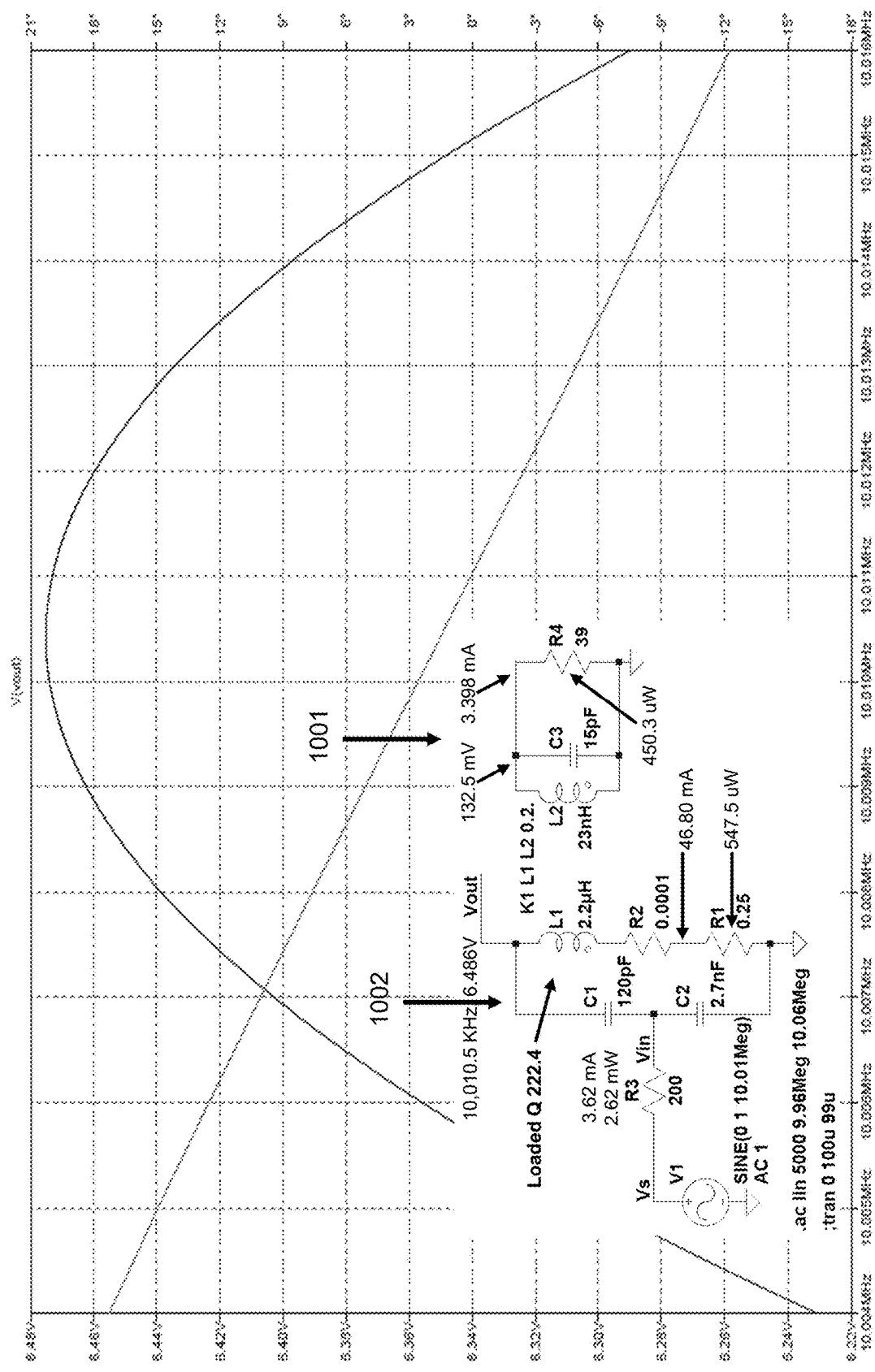
FIG. 10 shows amplitude and phase response with conditions identical to that of FIG. 5, except that the series resistance representing eddy current losses has been replaced by an external coupled parallel tuned circuit having component values thought to simulate conditions pertaining to FIG. 1 and physical conditions within the chest cavity.

FIG. 10 shows the amplitude and phase response of the same tuned circuit 303 as described in FIG. 5, showing the target loss R2 represented by 0.250 Ohms, with 1 Volt Vs applied. In FIG. 10, everything looks the same, but here, R2 is shown as zero Ohms, as if it were representing the no-target condition. In this case, however, there is an eddy current-producing target 1001 that is dissipating power and causing tuned circuit 1002 Q to be reduced to 222.4. It is still a circuit simulation, not a physical simulation, but it more closely represents the physical situation and provides some information about what is happening in target 1001. The plotted frequency range is much narrower than in the plot shown in FIG. 5, in order to see small frequency changes. In the schematic, the probe tuned circuit and carrier generator V1 are as shown as in FIG. 5. L2, C3, R4 and K1 were added to represent the eddy current target 1001 and mutual magnetic coupling.

The target is close enough that the magnetic field from L1 also exists at L2 and vice-versa. K1 represents the percentage of total magnetic flux generated by the current in L1 that exists within L2, and vice versa. The values of these four constants, distributed in the medium and in space, are shown in the schematic 1001, 1002, and are estimates based upon experimental results, human internal physiological data, and electromagnetic data and theory.

Figure 11:
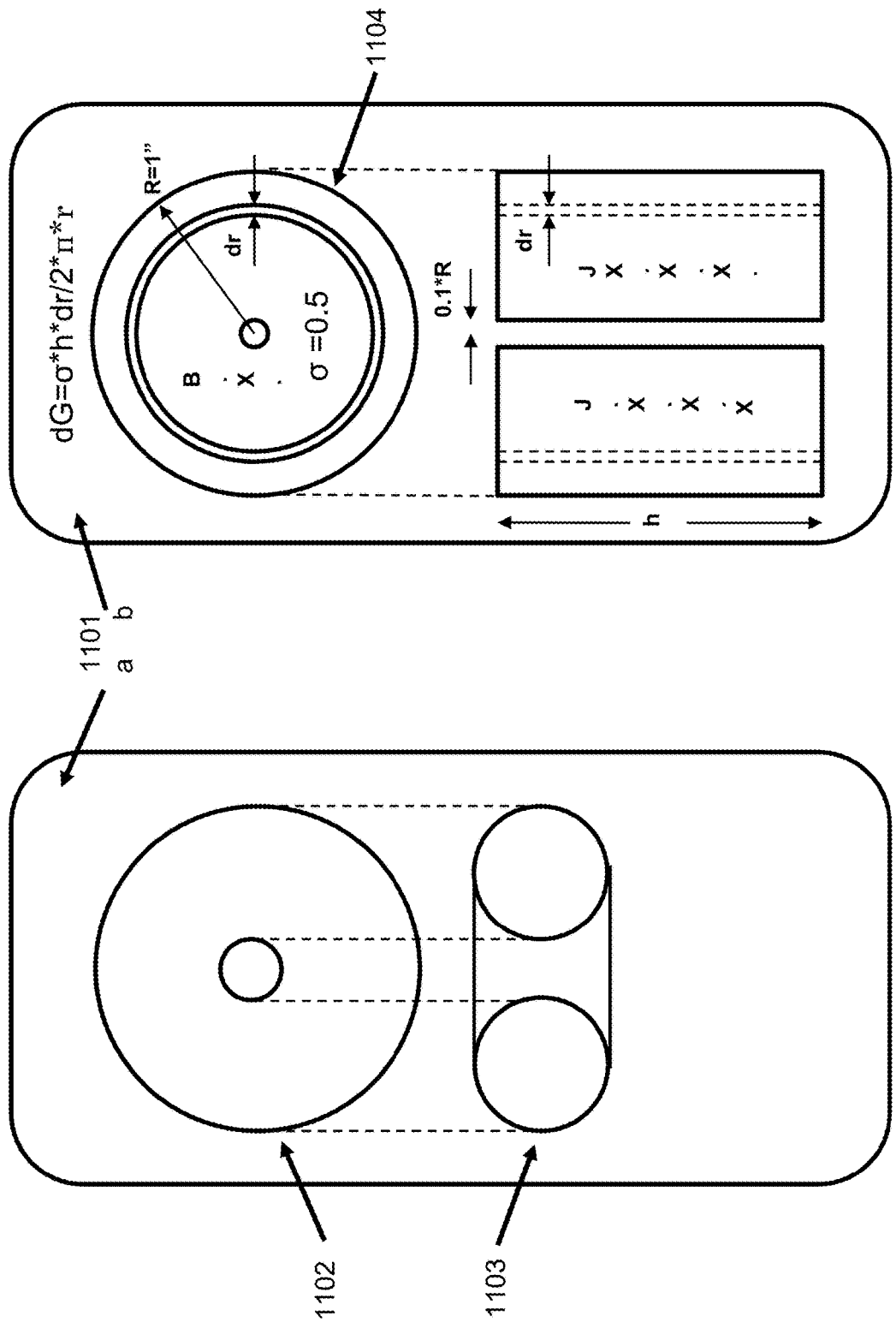
FIG. 11 supplements derivation of the external coupled parallel tuned circuit component values of FIG. 10, using electromagnetic theory and known properties of human chest cavity tissues.

K1, the magnetic coupling constant, was estimated by referring to published measured data of a similar configuration. Referring to FIG. 11, L2 was estimated by calculating the inductance of a thick single conductor loop 1102 whose volume occupies a considerable percentage of an imaginary 2 inch diameter, 2 inch depth cylinder existing in the chest cavity, the region where eddy currents induced by the chest-mounted high Q planar L1 (1002, 302) Probe exist.

In FIG. 11, 1101 represents the region of the chest cavity close to the position of inductor 103, 303. The shapes 1102 and 1103, a mechanical drawing, represent the region where significant eddy currents exist. Shape 1102 shows the "pictorial" view of the affected region behind electronic assembly 102, and shape 103 shows the side view of this cylindrical region. 1101b is also a mechanical drawing with the same two views, showing the direction of magnetic flux density "B" vectors and current density "J" vectors perpendicular to the page. The directions are indicated by "x" symbols. "h" is the height of the cylindrical region, which is in the direction between the front and rear of the chest cavity.

R4 was estimated by first researching the conductivity values of the various tissues and fluids within the above cylindrical region and estimating a very rough weighted value based upon the volume percentages of these tissues and fluids existing within the cylinder. This weighted conductivity average, shown as "σ" in FIG. 11, appears to be roughly 0.5 S/m (Siemens/meter). Assuming a roughly circular flow of current, based upon the position and orientation of the Probe inductor, the effective conductance, G, was calculated by an integration of dG of cylindrical circles from the outer radius 1104, "R" of this imaginary cylinder to 0.1 of this radius. A conductance value G of 0.0256 Siemens (mho) was obtained, corresponding to 39 Ohms total resistance.

C3 in FIG. 10 may be the stray capacitance between the region supporting eddy currents and surrounding regions. It was concluded by others that it has a negligible effect, and the simulations herein confirm their conclusion. 15 pF has a reactance of 1000 Ohms at 10.01 MHz, very high compared with other impedance values and in parallel with them. It changes the overall resonant frequency of the probe very slowly. This exact value was chosen to match the resonant frequency to what was obtained in the simulation with K1=0 and R2 0.25 (FIG. 5).

FIG. 10 plot shows the amplitude and phase response at the probe output Vout, 304b. Other information at resonance, here defined by zero phase difference between Vs and Vout was added to the schematic. Although the peak Vout, 6.475V, is at 10,010.45 KHz, the procedure is to measure this level at 0 degrees, which in this instance is 6.473V, negligibly different, at 10,011.0 KHz. As explained previously, Vout is related to the loaded Q. In FIG. 8, graph data point 804 shows where it is on the Vout curve. If the loaded Q is measured on the plot by the previously mentioned 3 dB method (widening the frequency range of display as necessary), it is found to be 222.4. If this number is added to the FIG. 8 Q curve graph data point 805, it is found to correspond to the same Rs value (R1+R2), 0.38 on the horizontal axis, as expected.

In FIG. 10, about 72% of the power coming from V1 is dissipated in R3, understandable, as the goal is to preserve Q of the tuned circuit, not transfer power efficiently. The remainder of the power is divided 55:45 between tuned circuit 1002 and target 1001. The latter draws about 3.4 mA from an induced 133 mV source. Only 450 uWatt is dissipated. The phase relationships are commensurate with what is expected from field theory, including, finally, the reduction of L1 current and the voltage across it owing to the induction at L2 and back induction to L1.

With the estimated L2 value shown (23 nH), the 1.45 Ohm inductive reactance is low compared with R4 at 39 Ohms; so there is relatively small phase shift, and a relatively small capacitive reactance is effectively induced in series with L1. Therefore, the resonant frequency shift upwards is very small as compared with no-target conditions (from 10,010.8 KHz to about 10,011.0 KHz). If R4 becomes 30 Ohms, as might happen when the heart is filled with blood (which has conductivity double that of the average value being used), it becomes closer to the inductive reactance of L2, increasing the phase shift. Therefore, the back-induced capacitive reactance becomes larger, causing the zero phase shift resonant frequency to increase to 10011.25 KHz. Vout drops to 5.899 VV, and total Q drops to 200.2. Checking FIG. 8 again, it can be seen from the graph data points 806 and 807 that total Q and Vout still track to the total loss ratio, in this case, 0.50 Ohm equivalent. Thus, by monitoring rate of change of resonant frequency with eddy current loss, data on target inductance could be used to determine additional target properties.

If the method of feedback controlled constant Vout is employed, V1 is varied to force Vout to the standard 9.603V. V1 would end up at 1.481V, the ratio of 9.603V to Vout in FIG. 10. All the voltages and currents would be multiplied by this factor, and all power dissipation values would be multiplied by the square of 1.481. The Q value of the tuned circuit would stay the same to become the principal measurement variable, as a hedge against non-linearity within the target. Even more significant is that keeping Vout and therefore I(L1) constant keeps penetration depth of the target medium constant.

The above analyses strongly indicate that the eddy current measurements described herein involve 10 MHz electric currents in the chest cavity amounting to about 5 mA. The International Commission on Non-Ionizing Radiation Protection (ICNIRP) restriction limit for current density within the human body from 100 KHz to 10 MHz is stated as follows: "Current density for head and trunk must not exceed f/100 mA/m^2", which for 10 MHz is 100,000 mA/m^2. Referring again to the magnetic field "B" vectors and current density "J" vectors in FIG. 11, the current area cross section is 1"×2"=0.0254 m×0.0508 m=0.00129 m^2. We have therefore 5 mA/0.00129 m^2=3875 mA/m^2, which is only 0.0388, or 3.88% of this established safety limit.

Figure 12:
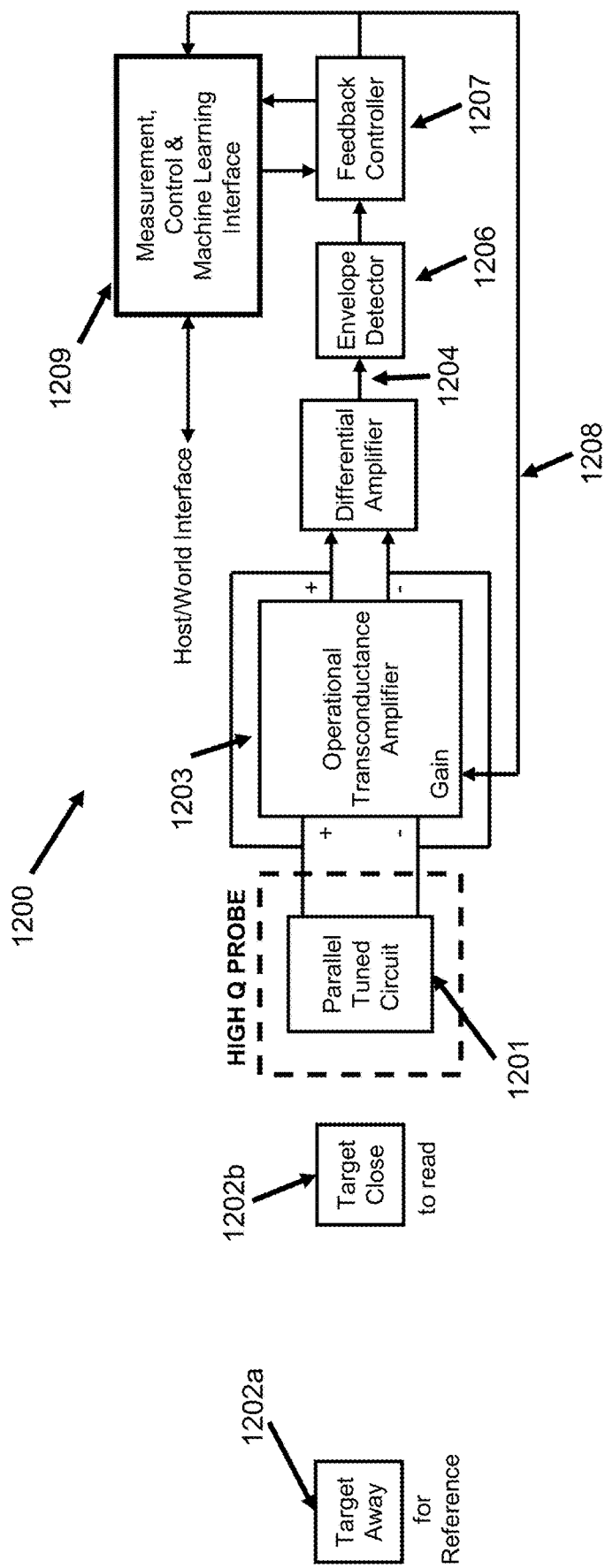
FIG. 12 shows an alternative to FIG. 3 example system architecture of an instrument to measure eddy currents using a coil inductor embedded in a negative resistance oscillator.

The implementation described with the aid of FIGS. 3 through 11 is robust, and permits the most comprehensive, accurate and rapid eddy current measurements, but it may not be suited for the very lowest power and extremely compact consumer products. FIG. 12 shows a method that may more successfully address these issues.

FIG. 12 shows an eddy current measurement method sometimes referred to as Negative Resistance, Conductance, or Impedance. It employs a probe parallel tuned circuit 1201 as the resonator in an oscillator circuit, as well as automatically adjusting the AC line current of this parallel tuned circuit to maintain a constant oscillator output level, regardless of the amount of tuned circuit Q reduction back-induced by the target 1202b. The Operational Transconductance Amplifier ("OTA"), which delivers a current instead of voltage output, functions together with Probe parallel tuned circuit 1201 to form an oscillator. When the gain of this amplifier 1203 is correct, oscillator output 1204 is maintained at some fiduciary level, such as the level it has with no target present, 1202a. This oscillator fiduciary output 1204 is set to a level that could be increased with additional AC line current to tuned circuit 1201, but specifically, this is not done. Therefore, when the output level needs to be adjusted to fiduciary level in response to decreased tuned circuit 1201 Q, the level will have a control system "signed error signal", indicating to the control system which direction takes it closer to the fiduciary level, without the need to move in a trial direction and reverse if necessary.

The rationale and design of the Probe parallel tuned circuit 1201 is similar to that of FIG. 3, including the possibility of switching in capacitors for frequency agility as described in the text. However, there may be no need for low impedance coupling, such as a tapped coil or tapped capacitors; as, depending upon the type of oscillator circuit used, all the line coupling may connect through the "top" and "bottom" of the tuned circuit.

The Differential Amplifier 1205 buffers OTA 1203 and converts current to voltage values. The Envelope Detector 1206 converts the AC sinusoidal signal to a dc voltage representing its amplitude. It may have a linear response, or logarithmic response in order to provide a greater amplitude range. The Feedback Controller 1207 varies its output voltage that adjusts OTA 1203 current gain until its sees the fiduciary level signal from the oscillator output 1204. The higher OTA 1203 current gain needed to return the oscillator output 1204 to its fiduciary signal level, the lower the tuned circuit 1201 Q has become, as loaded down by Target 1202b eddy current. Thus, this feedback control voltage is a measure of the eddy current amplitude in Target 1202b and its magnetic coupling to probe tuned circuit 1201. Inasmuch as the level of this amplifier gain feedback signal 1208, represents a measure of loss induced in Probe tuned circuit 1201 from Target 1202b eddy currents, this signal is fed also to the Measurement and Control module 1209, and thence to the data output display and memory.

Under some circumstances, the desired output level of oscillator 1204 may be the maximum value that can be obtained for any setting of its tuned circuit excitation current. Working only with oscillator signal amplitude, and looking for its peak, there would be no specific instantaneous information in the detected oscillator signal that tells the feedback controller whether to increase or decrease the OTA 1203 gain control level to increase oscillator signal level. This could occur if the fiduciary oscillator output level 1204 is set at or too close to the maximum achievable level for the oscillator supply voltage. Therefore, the tuned circuit excitation current must be incremented by OTA 1203 to one direction a small amount and then the other, with a bias toward the direction that increases oscillator signal output. When the peak level is reached, the readings for both incremented directions will be about equal, signaling the Controller to remove the incremental adjustment bias. If the OTA gain feedback voltage 1208 becomes too high, the Oscillator output voltage will begin to drop again.

As feedback controller 1207 sweeps OTA gain feedback voltage 1208 in either direction through the value that produces the peak oscillator output amplitude, it could signal the Measurement, Control, and Machine Learning Interface module 1209 at the moment of this peak. This would allow that module to acquire the OTA gain feedback voltage 1208 that represents the exact loaded Q of Probe tuned circuit 1201, a portion of which represents eddy current losses in Target 1202b. Alternatively, the feedback controller could continuously record both the OTA Gain feedback voltage 1208 it is delivering and the oscillator output amplitude 1204 it is receiving. It could then retrospectively (but almost immediately) select the OTA Gain feedback voltage 1208 corresponding to the peak oscillator output 1204 amplitude and deliver it to the Measurement, Control, and Machine Learning Interface module 1209 as a single data point. The delivery of data could repeat at rapid intervals.

Measurement, Control, and Machine Learning Interface module 1209 assists Feedback Controller 1207 to acquire accurate and timely data and provides interface to a Personal Smart Companion, Sensor Hub, smart phone, computers, and anything else in the world pertinent to data acquisition and reporting. This module could keep track of the data, such as recording whether it is gathered with or without a target present. It could speed up further acquisitions of the peak oscillator output amplitude value 1204 by storing its value. It could assist Feedback Controller 1207 to eliminate from the search field, feedback Gain voltage 1208 values that cannot apply to any value of target 1202*b* eddy currents, such as those below the level measured with no target present 1202*a*.

Additional circuit methods to reduce eddy current measurement size and power consumption have been developed and even offered for sale in a low cost integrated circuit device. Patent Application Publication (George Reitsma) US 2014/0247090 A1 describes the circuitry in this product, which uses the overall "negative impedance" approach previously filed by Olaf Machul in 2001 (US20030071638 A1) and Masahisa Niwa in 2007 (U.S. Pat. No. 8,432,169). Reitsma improves on power drain significantly through use of Class D amplifier technology for the OTA function and an H bridge to reverse polarity in the tuned circuit. All three of these publications concern themselves with proximity and separation measurements; none of them teach the use of eddy currents to measure target object properties, and none of them teach the use of high Q Probe tuned circuits to augment the study of targets with low conductivity and/or small eddy currents.

Figure 13:
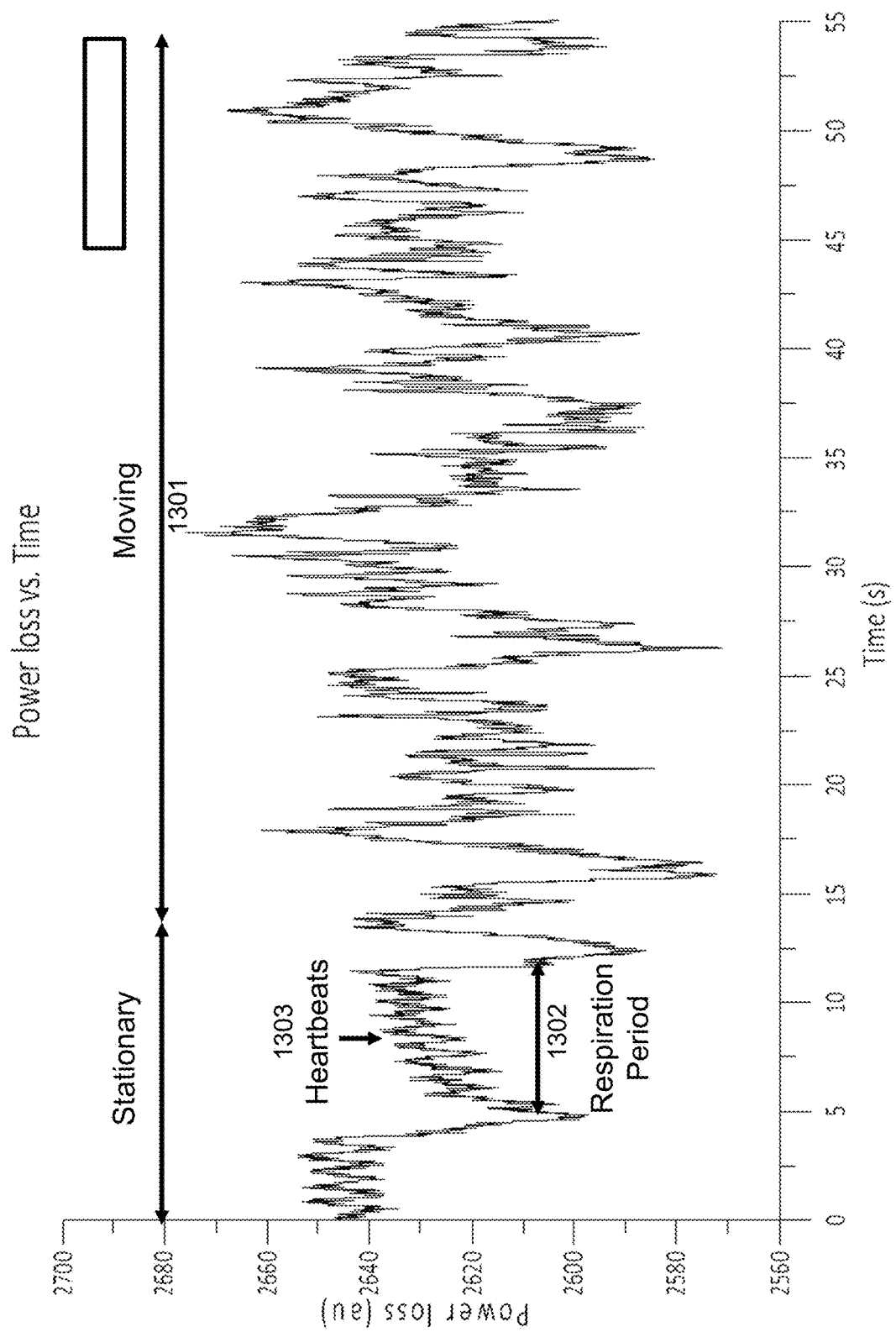
FIG. 13 shows comparison of heart and respiration rate data, obtained from equipment represented in FIG. 1, where the subject is first stationary then moving, and for which no filtering or machine learning is used.

An Eddy Current Measurement apparatus FIG. 1, including probe, constructed in the form of a patch that is attached to clothing, containing a flat spiral inductor and other components, as well as measurement and wireless communications circuitry, has been constructed, tested and found operational by the inventors as described above. As shown in FIG. 13, the system is subject to severe noise and artifacts when the Subject is moving 1301. As shown, the respiration data 1302 is severely impaired, and the heart rate data 1303 appears to be almost completely obscured.

Figure 14:
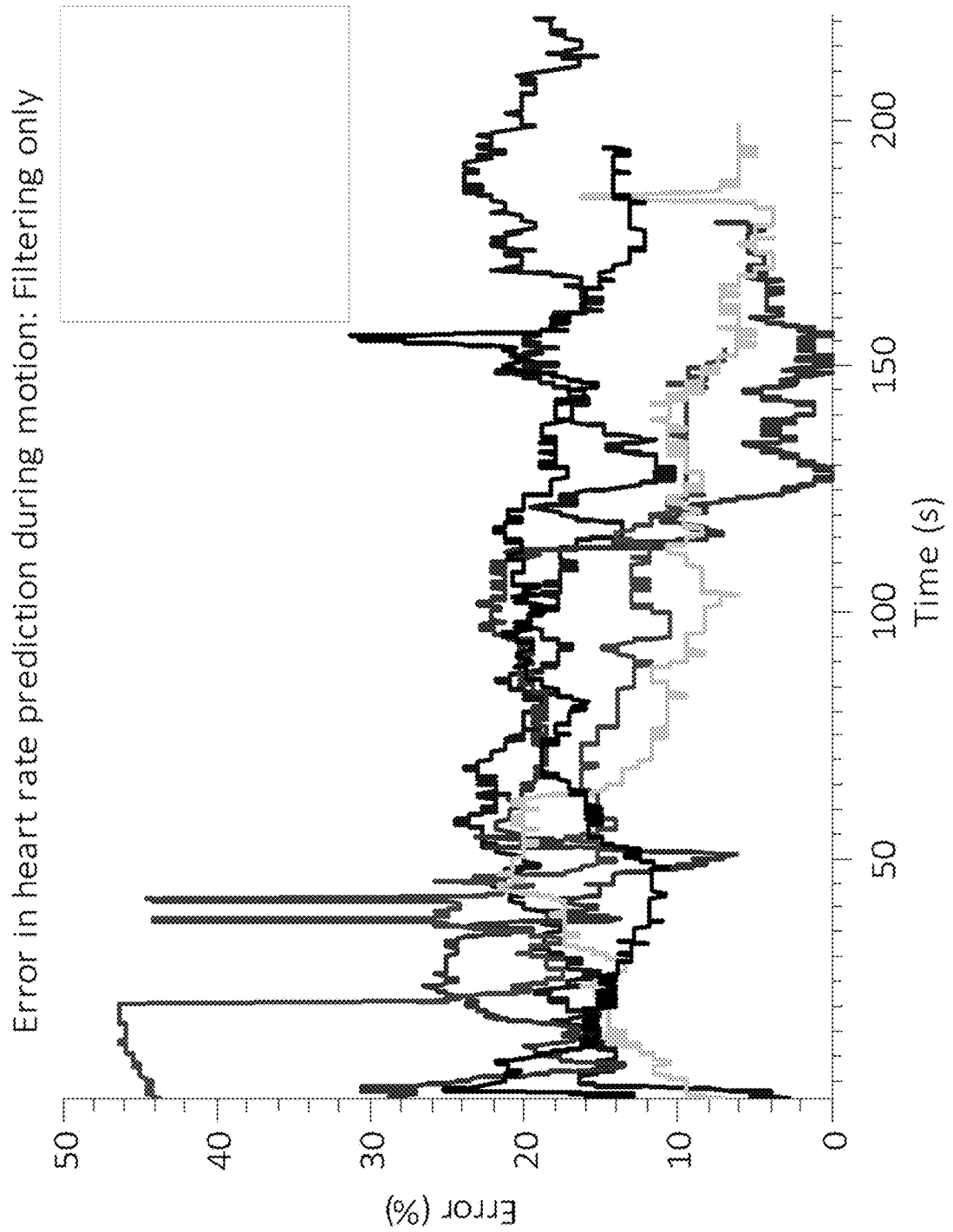
FIG. 14 shows heart and respiration rate data from equipment represented in FIG. 1, where the subject is in motion and for which signal filtering is used.
Figure 15:
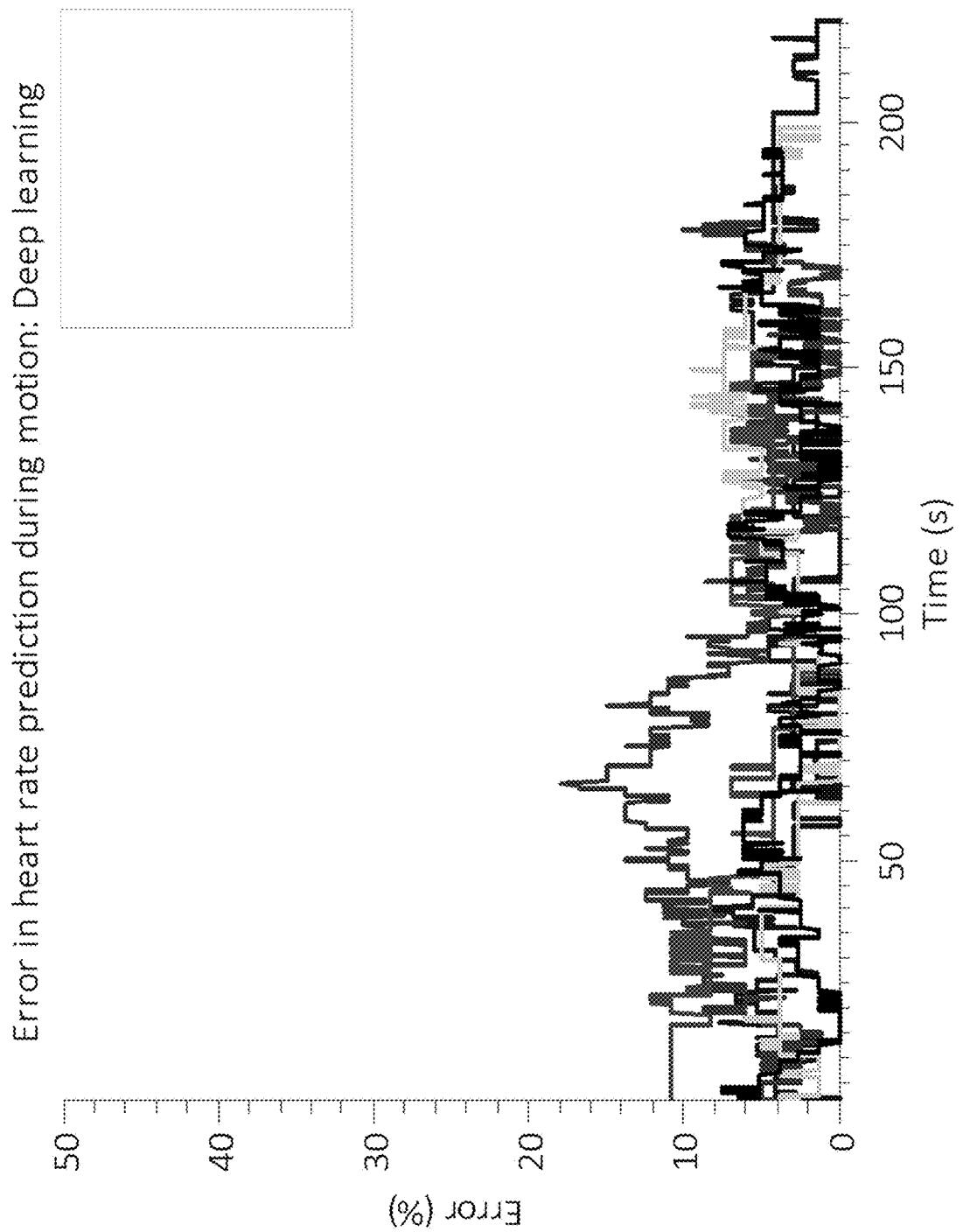
FIG. 15 shows heart and respiration rate data from equipment represented in FIG. 1, where the subject is in motion and for which signal filtering and deep machine learning is used.

Referring to FIG. 14, a small study was performed that reports cumulative heart rate measurement error rate over a period of 200 seconds for five subjects. One might expect that even with noisy data, the cumulative error rate would gradually diminish as there are an increasing number of samples to average. As shown, however, the noise is generally not Gaussian; the trend is down for only three of the subjects. The overall absolute value error is about 20%. FIG. 15 shows a similar experiment or even the same data, but after "Deep" Machine Learning has been applied. The improvement is pronounced, with error generally well under 5%, which may be clinically acceptable.

Figure 16:
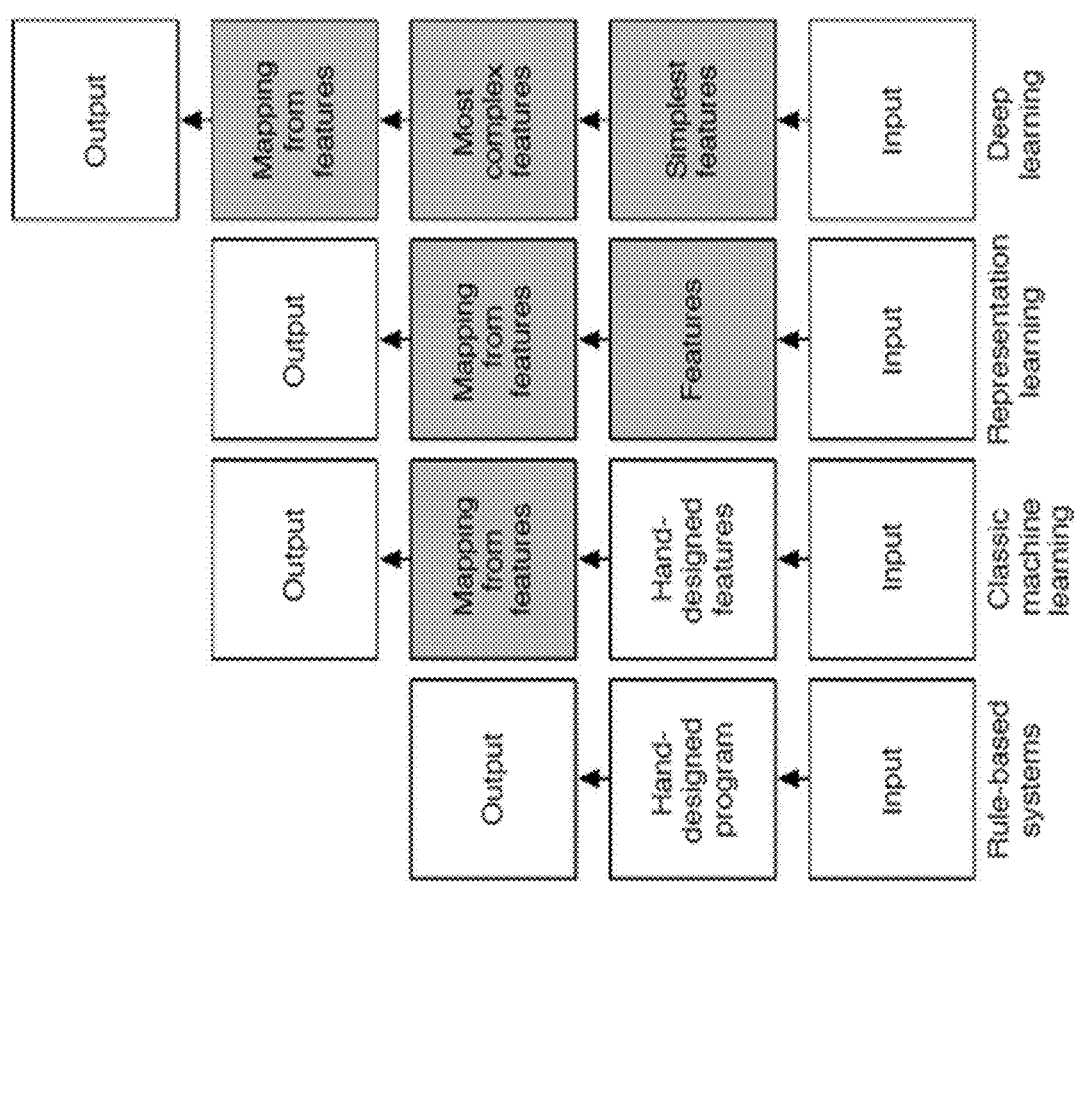
FIG. 16 supplements elementary tutorial information on machine learning techniques.

FIG. 16 compares a few variations of Deep Machine Learning. Machine learning is a collection of algorithms whose purpose is to create a mapping from data to insights. Deep learning is a powerful method to capture highly non-linear relationships It is commonly used for tasks like facial recognition by Google, Microsoft, Facebook, etc.

The details provided in the foregoing description and attached Appendix describe in part particular implementations of the systems for performing the functions explained in this disclosure. Other embodiments could be implemented in any other suitable manner. For example, the attached Appendix shows a particular module physical size and other physical configurations. This disclosure, appendix, and as-built example equipment report on and utilize a standard interface package—the size, as opposed to other sizes and shapes. These configurations are for illustration only. The attached appendix also includes the use of particular System blocks. Other embodiments could use different key system blocks, depending upon the implementation. Moreover, measuring pulse and respiration rate within the body only two examples of what the methods of this disclosure can perform.

It may be advantageous to set forth definitions of certain words and phrases used throughout this patent document. The term "couple" and its derivatives refer to any direct or indirect communication between two or more elements, whether or not those elements are in physical contact with one another. The terms "transmit," "receive," and "communicate," as well as derivatives thereof, encompass both direct and indirect communication. The terms "include" and "comprise," as well as derivatives thereof, mean inclusion without limitation. The term "or" is inclusive, meaning and/or. The phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, have a relationship to or with, or the like.

While this disclosure has described certain embodiments and generally associated methods, alterations and permutations of these embodiments and methods will be apparent to those skilled in the art. Accordingly, the above description of example embodiments does not define or constrain this disclosure. Other changes, substitutions, and alterations are also possible without departing from the spirit and scope of this disclosure.

What is claimed is:

1. A contactless and non-invasive physical properties measurement instrument utilizing very low-level eddy currents, comprising
   - a frequency agile monochromatic carrier generator coupled to a passive parallel tuned circuit probe containing a coil inductor and capacitors, wherein the probe has a quality factor (Q) value range from 50 to 500,
   - means to measure and adjust the generator frequency, wherein the frequency range comprises a resonant frequency of the probe and offsets to the resonant frequency, wherein the offsets comprise a range designed to measure loaded Q values of the probe,
   - a synchronous AM detector configured to measure and adjust the generator output level,
   - means to measure a phase difference between an input and output of the probe,
   - means to measure the output level of the probe, and
   - feedback loop circuitry, comprising a phase detector and a loop filter;
   - wherein the instrument is capable of applying a constant flux density to an eddy current target whose physical properties are being measured, by maintaining the probe output at a constant level while the input level is a monotonic and negative sloped function of the loaded Q value, and wherein an input voltage level is a linear function of an eddy current loss in the target, wherein the eddy current loss is represented by an equivalent resistance in series with a circuit loop of the probe.

2. The instrument of claim 1 wherein the probe is configurable to be maintained at a plurality of constant output voltages, creating a plurality of constant flux densities within the target, in order to determine how flux density affects eddy current loss.

3. The instrument of claim 1 configured to measure eddy currents via the loaded Q of the probe at resonance comprising
- monitoring only the output voltage, by first measuring said Q by setting the generator input voltage to a constant level,
- controlling the generator to the probe's resonant frequency using peaking of the output voltage and phase difference measurements between the input and the output voltages, and
- comparing said voltage output level with the generator at a frequency offset from probe's resonant frequency.

* * * * *